(12) United States Patent
Ogle et al.

(10) Patent No.: US 8,444,624 B2
(45) Date of Patent: May 21, 2013

(54) VASCULAR MEDICAL DEVICES WITH SEALING ELEMENTS AND PROCEDURES FOR THE TREATMENT OF ISOLATED VESSEL SECTIONS

(75) Inventors: Matthew F. Ogle, Fitchburg, WI (US); Jason C. Isenburg, Victoria, MN (US)

(73) Assignee: Vatrix Medical, Inc., Maple Grove, MN (US)

( * ) Notice: Subject to any disclaimer, the term of this patent is extended or adjusted under 35 U.S.C. 154(b) by 489 days.

(21) Appl. No.: 12/581,311

(22) Filed: Oct. 19, 2009

(65) Prior Publication Data

US 2011/0093000 A1 Apr. 21, 2011

(51) Int. Cl.
*A61M 31/00* (2006.01)
*A61M 29/00* (2006.01)

(52) U.S. Cl.
USPC ..................................... 604/509; 604/101.04

(58) Field of Classification Search
USPC ............. 604/101.01, 101.03, 101.04, 101.05, 604/509
See application file for complete search history.

(56) References Cited

U.S. PATENT DOCUMENTS

| | | |
|---|---|---|
| 5,000,734 A | 3/1991 | Boussignac et al. |
| 5,080,670 A | 1/1992 | Imamura et al. |
| 5,081,157 A | 1/1992 | Pomerantz |
| 5,147,514 A | 9/1992 | Mechanic |
| 5,376,114 A | 12/1994 | Jarvik |
| 5,512,291 A | 4/1996 | Li |
| 5,645,540 A | 7/1997 | Henniges et al. |
| 5,720,950 A | 2/1998 | Poiani et al. |
| 5,750,150 A | 5/1998 | Okazaki et al. |
| 5,752,974 A | 5/1998 | Rhee et al. |
| 5,834,449 A | 11/1998 | Thompson et al. |
| 5,876,744 A | 3/1999 | Della Valle et al. |
| 5,880,242 A | 3/1999 | Hu et al. |
| 5,955,097 A | 9/1999 | Tapolsky et al. |
| 5,968,500 A | 10/1999 | Robinson |
| 6,029,671 A | 2/2000 | Stevens et al. |
| 6,063,770 A | 5/2000 | Falcon |
| 6,391,538 B1 | 5/2002 | Vyavahare et al. |
| 6,432,922 B1 | 8/2002 | Brunck et al. |
| 6,437,004 B1 | 8/2002 | Perricone |
| 6,444,234 B1 | 9/2002 | Kirby et al. |
| 6,463,317 B1 | 10/2002 | Kucharczyk et al. |
| 6,469,053 B1 | 10/2002 | Romanczyk, Jr. et al. |

(Continued)

FOREIGN PATENT DOCUMENTS

WO 01/41735 A2 6/2001
WO 2007/064152 A1 6/2007

OTHER PUBLICATIONS

Search Report and Written Opinion for International Application No. PCT/US2010/053017, dated Dec. 13, 2010.

(Continued)

*Primary Examiner* — Nicholas Lucchesi
*Assistant Examiner* — Nathan R Price
(74) *Attorney, Agent, or Firm* — Dardi & Herbert, PLLC; Peter S. Dardi

(57) ABSTRACT

Devices for the isolation of a selected portion of a vessel are described. In some embodiments, the device comprises an introducer sheath and a sealing catheter that are movable relative to each other to create an isolated volume with adjustable size and location. The methods for the treatment of vascular aneurysms using the devices are described. The treatment is achieved through the delivery of an effective amount of stabilization agent to an isolated volume that encompass the aneurysm. The device optionally has an aspiration means to improve the effectiveness of the treatment.

15 Claims, 8 Drawing Sheets

U.S. PATENT DOCUMENTS

| | | | |
|---|---|---|---|
| 6,471,723 | B1 | 10/2002 | Ashworth et al. |
| 6,471,973 | B1 | 10/2002 | Perrier et al. |
| 6,517,824 | B1 | 2/2003 | Kohn et al. |
| 6,599,448 | B1 | 7/2003 | Ehrhard, Jr. et al. |
| 6,608,040 | B1 | 8/2003 | Lin et al. |
| 6,610,320 | B2 | 8/2003 | Schmitz et al. |
| 6,663,589 | B1 | 12/2003 | Halevy |
| 6,712,831 | B1 | 3/2004 | Kaplan et al. |
| 6,747,059 | B1 | 6/2004 | Romanczyk, Jr. et al. |
| 6,793,644 | B2 | 9/2004 | Stenzler |
| 6,800,080 | B1 | 10/2004 | Bates |
| 6,800,292 | B1 | 10/2004 | Murad |
| 6,929,626 | B2 | 8/2005 | DiCarlo et al. |
| 6,929,633 | B2 | 8/2005 | Evans et al. |
| 6,979,347 | B1 | 12/2005 | Wu et al. |
| 7,008,441 | B2 | 3/2006 | Zucker |
| 7,063,838 | B1 | 6/2006 | Franano |
| 7,166,120 | B2 | 1/2007 | Kusleika |
| 7,201,918 | B2 | 4/2007 | Cruise |
| 7,252,834 | B2 | 8/2007 | Vyavahare et al. |
| 7,323,169 | B2 | 1/2008 | Goldenberg et al. |
| 7,351,421 | B2 | 4/2008 | Sung et al. |
| 7,503,904 | B2 | 3/2009 | Choi |
| 7,713,543 | B2 | 5/2010 | Vyavahare et al. |
| 2001/0018569 | A1 | 8/2001 | Erbel et al. |
| 2001/0029349 | A1 | 10/2001 | Leschinsky |
| 2002/0016565 | A1 | 2/2002 | Zadno-Azizi et al. |
| 2003/0078659 | A1 | 4/2003 | Yang |
| 2003/0170287 | A1 | 9/2003 | Prescott |
| 2003/0171287 | A1 | 9/2003 | Morishita et al. |
| 2003/0228364 | A1 | 12/2003 | Nathan |
| 2003/0232895 | A1 | 12/2003 | Omidian et al. |
| 2004/0153145 | A1 | 8/2004 | Simionescu et al. |
| 2005/0079202 | A1 | 4/2005 | Chen et al. |
| 2005/0245893 | A1 | 11/2005 | Leschinsky |
| 2006/0025853 | A1 | 2/2006 | Evans et al. |
| 2006/0034925 | A1 | 2/2006 | Au et al. |
| 2006/0041269 | A1 | 2/2006 | Horrigan |
| 2006/0159641 | A1 | 7/2006 | Girardot et al. |
| 2006/0212112 | A1 | 9/2006 | Evans et al. |
| 2006/0240066 | A1 | 10/2006 | Vyavahare et al. |
| 2007/0150041 | A1 | 6/2007 | Evans et al. |
| 2007/0162106 | A1 | 7/2007 | Evans et al. |
| 2007/0276477 | A1 | 11/2007 | Lee et al. |
| 2007/0281026 | A1 | 12/2007 | Vyavahare et al. |
| 2007/0282422 | A1 | 12/2007 | Biggs et al. |
| 2007/0293937 | A1 | 12/2007 | Biggs et al. |
| 2008/0039923 | A1 | 2/2008 | Taylor et al. |
| 2008/0294233 | A1 | 11/2008 | Staniloae et al. |
| 2009/0076447 | A1 | 3/2009 | Casas et al. |
| 2009/0186370 | A1 | 7/2009 | Ogle et al. |
| 2009/0214654 | A1 | 8/2009 | Isenburg et al. |
| 2010/0016833 | A1 | 1/2010 | Ogle et al. |

OTHER PUBLICATIONS

Adams et al., "Crosslink formation in porcine valves stabilized by dye-mediated photooxidation," J Biomed Mater Res 57(4): 582-587 (2001).

Abstract—Ammoury et al., "Jejunal absorption, pharmacological activity, and pharmacokinetic evaluation of indomethacin-loaded poly(d,l-lactide) and poly(isobutylcyanoacrylate) nanocapsules in rats," Pharm Res 1991; 8(1):101-105.

Brem et al., "Interstitial chemotherapy with drug polymer implants for the treatment of recurrent gliomas," J. Neurosurgery, 1991;74(3): 441-446.

Calvo et al., "Long-circulating PEGylated polycyanoacrylate nanoparticles as new drug carrier for brain delivery," Pharm Res 2001;18(8):1157-1166.

Choke et al., "A review of biological factors implicated in abdominal aortic aneurysm rupture," Eur J Vasc Endovasc Surg 30: 227-244 (2005).

Connolly et al., "Triglycidylamine crosslinking of porcine aortic valve cusps or bovine pericardium results in improved biocompatibility, biomechanics, and calcification resistance," Am J Pathol 2005;166(1):1-13.

Daugherty et al., "Mouse models of abdominal aortic aneurysms," Arterioscler. Throat. Vasc. Biol. 2004;24:429-434.

Dawson et al., "Pharmacotherapy of abdominal aortic aneurysms," Curr Vasc Pharmacol, 2006;4:129-149.

Gershlick, "Endovascular manipulation to restrict restenosis," Vascular Medicine 1998; 3:177-188.

Gertz et al., "Aneurysm of the Rabbit Common Carotid Artery Induced by Periarterial Application of Calcium Chloride In Vivo," J. Clin. Invest. 1988, 81:649-656.

Isenburg et al., "Elastin stabilization for treatment of abdominal aortic aneurysms," Circulation 2007;115:1729-1737.

Isenburg et al., "Structural requirements for stabilization of vascular elastin by polyphenolic tannins," Biomaterials, 2006;27:3645-3651.

Isenburg et al., "Tannic acid treatment enhances biostability and reduces calcification of glutaraldehyde fixed aortic wall," Biomaterials, 2005;26:1237-1245.

Isenburg et al., "Elastin stabilization in cardiovascular implants: Improved resistance to enzymatic degradation by treatment with tannic acid," Biomaterials, 2004;25:3293-3302.

Jorge-Herrero et al., "Calcification of pericardial tissue pretreated with different amino acids," Biomaterials 1996;17(6): 571-575.

Abstract—Kageyama et al., "Ultrastructural visualization of elastic fibers with a tannate—metal salt method," Histochem J 1985;17(1):93-103.

Kasyanov et al., "Tannic acid mimicking dendrimers as small intestine submucosa stabilizing nanomordants," Biomaterials, 2006;27:745-751.

Meuris et al., "Porcine Stentless Bioprostheses: Prevention of Aortic Wall Calcification by Dye-Mediated Photo-Oxidation," Artif Organs 2003;27(6):537-543.

OCI Therapeutics ClearWay (TM) RX product literature, Atrium Medical Corporation, 2007, 12 pages.

Abstract—Paavola et al., "Controlled release of lidocaine from injectable gels and efficacy in rat sciatic nerve block," Pharm Res 1995;12(12)1997-2002.

Petite et al., "Cytocompatibility of calf pericardium treated by glutaraldehyde and by acyl azide methods in an organotypic culture model," Biomaterials 1995;16(13): 1003-1008.

Abstract—Petite et al., "Use of diphenylphosphorylazide for cross-linking collagen-based biomaterials," J Biomed Mater Res 1994;28(2):159-165.

Abstract—Petite et al., "Use of the acyl azide method for cross-linking collagen-rich tissues such as pericardium," J Biomed Mater Res 1990;24(2):179-187.

Prabha et al., "Critical determinants in PLGA/PLA nanoparticle-mediated gene expression," Pharm Res 2004;21 (2):354-364.

Abstract—Simionescu et al., "Lysine-enhanced glutaraldehyde crosslinking of collagenous biomaterials," J Biomed Mater Res 1991;25(12):1495-1505.

Simionescu et al., "Galloylglucoses of low molecular weight as mordant in electron microscopy. I. Procedure, and evidence for mordanting effect," J Cell Biol 1976;70(3):608-621.

Sung et al., "Crosslinking of biological tissues using genipin and/or carbodiimide," J Biomed Mater Res 2003;64A:427-438.

Sung et al., "Mechanical properties of a porcine aortic valve fixed with a naturally occurring crosslinking agent," Biomaterials 1999;20:1759-1772.

Van Wachem et al., "In vivo behavior of epoxy-crosslinked porcine heart valve cusps and walls," J Biomed Mater Res 2000;53(1):18-27.

Vyavahare et al., "Elastin calcification and its prevention with aluminum chloride pretreatment," Am J Pathol 1999;155(3):973-982.

VASCULAR MEDICAL DEVICES WITH SEALING ELEMENTS AND PROCEDURES FOR THE TREATMENT OF ISOLATED VESSEL SECTIONS

FIELD OF THE INVENTION

The inventions, in general, are related to devices with sealing balloons that can adjustably isolate a section of a vessel to create an adjustable isolated volume. A sealing balloon associated with an introducer sheath can be used to seal a portion of a blood vessel through the femoral artery in a patient's leg. The inventions are further related to the treatment of vascular aneurysms or other vascular diseases by using the devices to isolate the aneurysm for localized delivery of treatment compositions. Before the delivery of the treatment composition, the blood in the isolated volume including the aneurysm or a portion thereof can be aspirated to reduce the pressure on the aneurysmal wall and to prevent dilution of the composition.

BACKGROUND

Aneurysms are degenerative diseases characterized by destruction of arterial architecture and subsequent dilatation of the blood vessel that may eventually lead to fatal ruptures. Some common locations for aneurysms include the abdominal aorta (abdominal aortic aneurysm, AAA), thoracic aorta, and brain arteries. In addition, peripheral aneurysms of the leg, namely the popliteal and femoral arteries are prevalent locations of this vascular pathology. The occurrence of such peripheral aneurysms appears to be strongly associated with the presence of aneurysms in other locations, as it has been estimated that 30 to 60% of peripheral aneurysm patients also have an AAA.

Aneurysms grow over a period of years and pose great risks to health. Aneurysms have the potential to dissect or rupture, causing massive bleeding, stroke, and hemorrhagic shock, which can be fatal in more than 80% of cases. AAAs are a serious health concern, specifically for the aging population, being among the top ten causes of death for patients older than 50. The estimated incidence for abdominal aortic aneurysm is about 50 in every 100,000 persons per year. Approximately 60,000 operations are performed each year in the U.S. for AAAs alone. In children, AAAs can result from blunt abdominal injury or from Marfan's syndrome, a defect in elastic fiber formation in walls of major arteries, such as the aorta.

Aneurysms can be caused by any of a large class of degenerative diseases and pathologies including atherosclerotic disease, defects in arterial components, genetic susceptibilities, and high blood pressure, among others, and can develop silently over a period of years. The hallmarks of aneurysms include enzymatic degradation of vascular structural proteins such as elastin, inflammatory infiltrates, calcification, and eventual overall destruction of the vascular architecture.

Current methods of treatment for diagnosed aneurysms are generally limited to invasive surgical techniques. After initial diagnosis of a small aneurysm, the most common medical approach is to follow up the development of the aneurysm and after reaching a pre-determined size (e.g., about 5 cm in diameter), surgical treatment is applied. Current surgical treatments generally are limited to either an endovascular stent graft repair or optionally complete replacement of the diseased vessel with a vascular graft. While such surgical treatments can save lives and improve quality of life for those suffering aneurysm, dangers beyond those of the surgery itself still exist for the patient due to possible post-surgery complications (e.g., neurological injuries, bleeding, or stroke) as well as device-related complications (e.g., thrombosis, leakage, or failure). Moreover, depending upon the location or anatomy of the aneurysm, the danger of an invasive surgical procedure may outweigh the possible benefits of the procedure, for instance in the case of an aneurysm deep in the brain, leaving the sufferer with very little in the way of treatment options. Moreover, surgical treatments may not always provide a permanent solution, as vascular grafts can loosen and dislodge should the aneurysm progress following the corrective surgery.

Generally, most of the current treatment options for aneurysm are mechanical bridges. For some patients, the particular nature of the aneurysm or the condition of the patient makes the patient unsuitable for graft repair.

Aneurysm is not the only condition for which enzymatic degradation of structural proteins is a hallmark. Other conditions in which structural protein degradation appears to play a key role include Marfan syndrome, supravalvular aortic stenosis, and chronic obstructive pulmonary disease (COPD). For those afflicted, such conditions lead to, at the very least, a lowered quality of life and often, premature death.

SUMMARY OF THE INVENTION

In a first aspect, the invention pertains to a medical device for sealing a vessel. The device comprises a shaft having a proximal end, a distal end and a sealing element attached at or near the distal end of the shaft. The sealing element comprises an extendable element that can be transformed between a lower profile configuration and an extended configuration. In some embodiments, the extendable element can comprise a flexible, fluid impermeable membrane that has in the extended configuration a distal end, a proximal end and a generally cylindrical surface between the distal end and the proximal end. The extendable element can comprise a balloon. The distal end and the proximal end of the extendable element can be concave or cupped.

In some embodiments, the extendable element comprises a balloon that is inflated in the extended configuration and un-inflated in the lower profile configuration. The shaft of the device has a balloon lumen in fluid communication with the balloon and a proximal port. The shaft of the device can comprise a fluid exchange lumen extending from at or near the proximal end to an opening proximal to the extendable element. In some embodiments, the extendable element of the device comprises a self-extending support that interfaces with the membrane and transitions the extendable element between the lower profile configuration and the extended configuration when the support is unconstrained.

In a second aspect, the invention pertains to an introducer sheath. The introducer sheath comprises a shaft having a proximal end, a distal end, a distal end opening, a main lumen, and a balloon lumen. In general, the shaft can have a length no more than about 15 to 50 centimeters. The main lumen of the introducer sheath extends from the proximal end to the distal end opening of the shaft, having an inner diameter perpendicular to the axis of the lumen that is at least about 2.5 millimeters and no more than about 5 millimeters at each point along the lumen. A sealing balloon can be attached at or near the distal end of the shaft to form a balloon interior. The sealing balloon can comprise a compliant polymer in an approximately cylindrically symmetrical placement around the shaft. The balloon is transformable between a lower profile un-inflated configuration and an expanded inflated configuration. The device also can comprise a proximal fitting comprising a first port and a second port that is connected to the proximal end of the shaft. The first port can be in fluid communication with the main lumen and the distal end opening of the shaft. The second port can be in fluid communication with the balloon lumen. The balloon lumen extends between the balloon interior and the proximal fitting with an opening in the shaft providing fluid communication between the balloon interior and the balloon lumen.

In some embodiments, an aspiration apparatus can be operably connected to the first port of the introducer sheath. The aspiration apparatus can comprise a syringe. In some embodiments, a delivery element is operably connected to the first port wherein the delivery element comprises a stabilizing liquid that reacts with vessel tissue to stabilize the tissue that can be delivered through the main lumen of the sheath. In some embodiments, a delivery device comprises an inflation liquid can be operably connected to the second port. The outer diameter of the shaft of the sheath can be from about 3 mm to about 6 mm. In some embodiments, the shaft has a length no more than about 30 centimeters.

In a third aspect, the invention pertains to a device for treating an isolated portion of a blood vessel. The device can comprise a sealing catheter and an introducer sheath. The sealing catheter comprises a proximal end, a distal end, a first sealing element, at least one lumen extending from the proximal end to at or near the distal end, and at least one fluid exchange opening in fluid communication with the lumen of the sealing catheter. The lumen of the first catheter connects with a port at its proximal end that is in fluid communication with the lumen and the exchange opening. The first sealing element is attached distal to the fluid exchange opening at or near the distal end of the first catheter. The first sealing element comprises a first extendable element that can be transformed between a lower profile configuration and an extended configuration.

The introducer sheath of the device comprises a proximal end, a distal end, a fitting, and a second sealing element attached at or near the distal end of the introducer sheath. The second sealing element comprises a second extendable element that can be transformed between a lower profile configuration and an extended configuration. The sealing catheter extends through the fitting of the introducer sheath such that the fitting allows the relative movement of the sealing catheter and the introducer sheath.

In some embodiments, the first extendable element comprises a first balloon having an interior that is inflated in the extended configuration and un-inflated in the lower profile configuration. The first catheter comprises a first balloon lumen in fluid communication with the balloon interior and a proximal inflation port. The inflated first balloon has a generally cylindrical shape comprising distal and proximal ends that are concave or cupped in shape to ensure flexible and tight contact against the wall of the vessel. In one embodiment, the first balloon comprises a compliant polymeric material. In some embodiments, a delivery element is operably connected to the port of the first catheter. The delivery element can comprise a stabilizing liquid that reacts with vessel tissue to stabilize the tissue and is in fluid communication with the fluid exchange opening through the lumen and the port of the sealing catheter.

In some embodiments, the second extendable element comprises a second balloon having an interior that is inflated in the extended configuration and un-inflated in the lower profile configuration. The introducer sheath can comprise a second balloon lumen in fluid communication with the second balloon interior and a proximal inflation port. In some embodiments, the introducer sheath comprises a main lumen that extends between the proximal end and the distal opening of the introducer sheath that is operably connected to and in fluid communication with a proximal port of the introducer sheath. In one embodiment, the proximal port is operably connected to an aspiration apparatus. In one embodiment, the fitting of the introducer sheath is the main lumen of the introducer sheath and the sealing catheter coaxially resides inside the main lumen of the introducer sheath.

In a fourth aspect, the invention pertains to a method for treating an isolated portion of a blood vessel. The method comprises first positioning an isolation device within the blood vessel to select a portion of the blood vessel for isolation. The isolation device comprises a first extendable element, a second extendable element, a first fluid exchange opening, a second fluid exchange opening, a first fluid exchange lumen, a second fluid exchange lumen, a first proximal connection port and a second proximal connection port, the two fluid exchange openings being between the first extendable element and the second extendable element. The extendable elements of the isolation device are movable relative to each other within the vessel to select a portion of the vessel for isolation. A first flow path of the isolation device extends from the first proximal connection port through the first fluid exchange lumen to the first fluid exchange opening. A second flow path of the isolation device extends from the second proximal connection port through the second fluid exchange lumen to the second fluid exchange opening. After the isolation device is placed inside the blood vessel, additional steps can follow to conduct the treatment, including: isolating the selected portion of the blood vessel using the isolation device that is positioned within the vessel with the two extendable elements contacting the walls of the vessel to form the isolated portion; aspirating fluid from the isolated portion through the second flow path; and delivering a therapeutic composition to the isolated segment of the blood vessel through the first flow path after aspiration of fluid from the isolated portion of the blood vessel. The first flow path and second flow path can be the same flow path with the first fluid exchange lumen and the second fluid exchange being the same lumen and the openings can similarly be the same.

In some embodiments, the second extendable element is placed in the femoral artery in one of the legs of a patient and the first extendable element is placed in the aorta below the renal arteries. An additional sealing device can be deployed in the femoral artery in the other leg of the patient to isolate a "Y" shaped portion of the blood vessel along with the first and the second extendable elements. In some embodiments, the therapeutic composition used in the treatment comprises an elastin stabilizing composition. The isolated portion of the blood vessel comprises an aneurysm. The volume of the aneurysm is generally reduced following aspiration by at least about 10 percent wherein the volume of the aneurysm is evaluated as the excess volume in comparison with a corresponding healthy vessel lacking an aneurysm. In one embodiment, the therapeutic composition used in the treatment further comprises a contrast agent.

In some embodiments, the step of delivering the therapeutic composition is repeated with a different composition. The delivery of one therapeutic composition comprises the delivery of an elastin stabilization composition and the delivery of other therapeutic composition comprises the delivery of a collagen stabilization composition. In one embodiment, the collagen stabilization composition comprises glutaraldehyde, carbodiimides, photo-oxidation agent, genipin, epoxies, and azide esters. In some embodiment, the therapeutic composition can further comprise a delivery vehicle comprising a pentagalloylglucose gel, a hydrogel, nanoparticles, or a combination thereof.

In some embodiments, the treatment method further comprises a pretreatment step before the delivery of the therapeutic composition. The pretreatment step comprises the delivery of a thrombolytic composition to break up thrombus in the isolated blood vessel. The aspiration and delivery steps can be performed at least partially simultaneously with the rate of aspiration consistently greater than the delivery.

In a fifth aspect, the invention pertains to a method for treating an isolated portion of a femoral artery. The method comprises the steps of isolating a portion of the femoral artery using a sealing introducer sheath positioned with its distal end within the femoral artery through an access point. The sealing introducer sheath comprises a distal extendable element, a distal fluid exchange opening, a main lumen, a proximal connection port. A flow path extends from the proximal connection port through the main lumen to the distal fluid exchange opening. The extendable element contacts the femoral artery wall to isolate the selected portion of the femoral artery. In one embodiment, the isolated selected portion of the femoral artery is below the access point of the femoral artery. The method can further comprise a step of performing a procedure within the isolated portion of the femoral artery through the delivery of an instrument through the main lumen of the sheath.

DETAILED DESCRIPTION OF PREFERRED EMBODIMENTS

Figure 1:
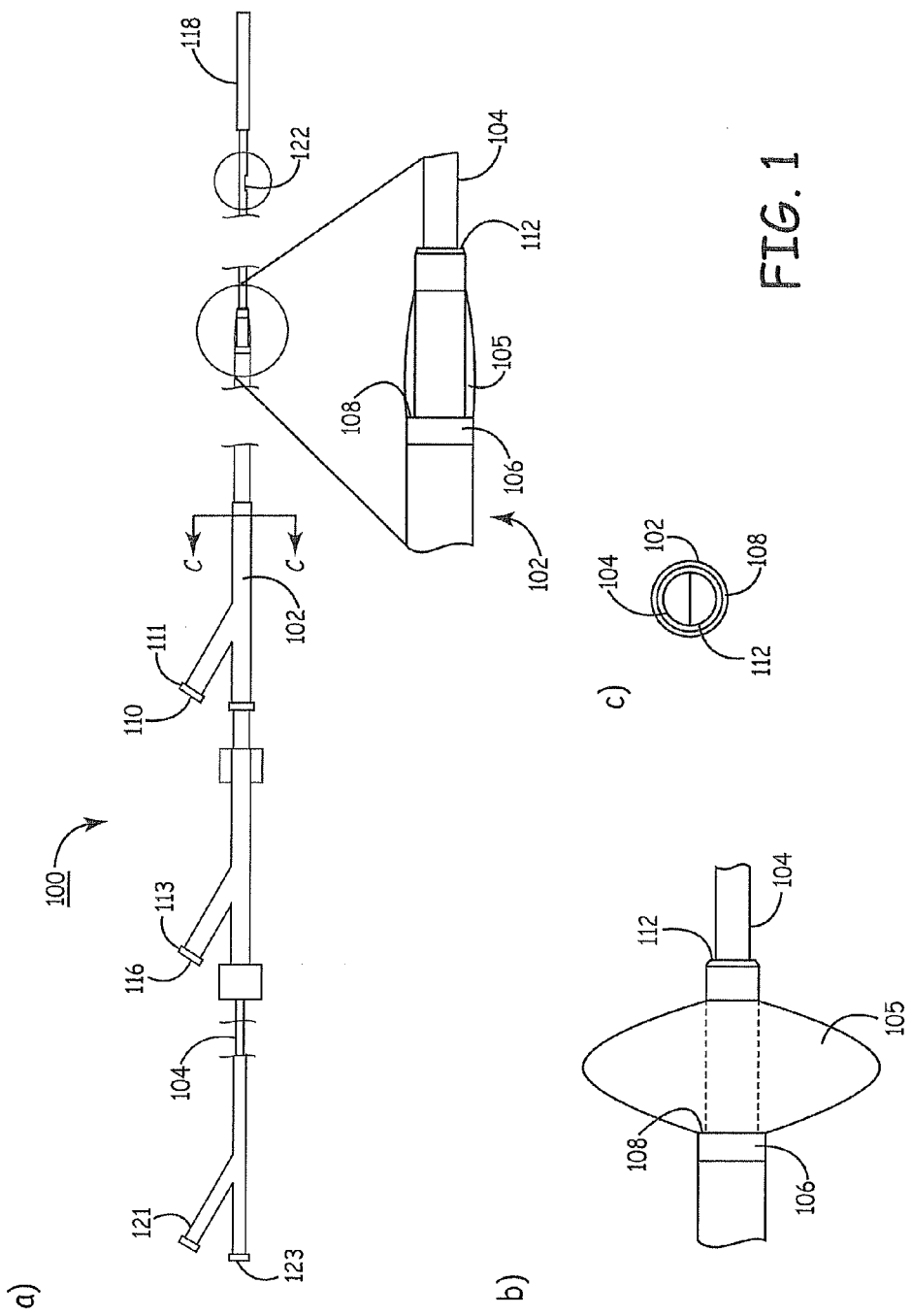
FIG. 1 is (a) a schematic side view of a sealing device with an enlarged view of the distal portion of a sealing introducer sheath, (b) the enlarged view of the distal portion of the sealing introducer sheath of the sealing device when a distal balloon is inflated, and (c) a cross sectional view of the lumens of the introducer sheath.

Vascular devices described herein provide for the sealing of selected portions of blood vessels to be able to provide for desired treatment. In some embodiments, the devices described herein provide for the isolation of a volume around a selected portion of a blood vessel through a less invasive procedure that accesses the blood vessel through the patient's vasculature or other vessel. For the sealing of two ends of a selected portion of a vessel, the devices can comprise two extendable elements that are movable relative to each other. The volume and location of the isolated vessel portion therefore can be adjusted based on the relative positions of the two extendable elements. When treating aneurysm for example, one of the extendable elements can be placed in femoral artery close to the vessel access point where the device enters the vessel while the other extendable element can be placed in aortic artery beyond the site of aneurysm or a significant portion thereof. When the two extendable elements are deployed, an isolated volume encompassing the aneurysm is created between the two extendable elements. The extendable element placed close to the vessel access point can be called the proximal extendable element, which may be part of an introducer sheath. The extendable element placed beyond the site of aneurysm can be called the distal extendable element, which may be carried on a sealing catheter. Improved designs of the extendable element of the sealing catheter such as a sealing balloon for placement in the aorta provide for good sealing properties with reduced risk of damaging potentially vulnerable vessel tissue. The sealing introducer sheath provides considerable versatility to the procedure, and the sealing introducer sheath can be effectively used without the sealing catheter component for the performance of procedures, for example, in the femoral artery.

One or two sealing introducer sheath can be used separately for sealing the femoral artery or arteries in conjunction with the sealing balloon placed in the aorta. When two sealing introducer sheaths are used, one sealing introducer sheath can be placed in femoral artery of one of the legs of the patient, the second sealing introducer sheath can be placed in femoral artery of the other leg of the patient. The isolated portion of the blood vessel therefore is defined by the extendable elements of the two sealing introducer sheaths placed in femoral arteries and the sealing balloon in aorta, thus encompassing a large portion of the blood vessel. While the application of the devices in femoral arteries and aorta is discussed, the devices can be used in other vessels to form isolated portions with a selected size.

The relatively large isolated portion of the blood vessel between the extendable elements can be advantageous during the treatment of aneurysm. Because although certain portion of the blood vessel exhibits particularly apparent characteristics of aneurysm while the rest of the blood vessel appear to be normal, the normal looking blood vessel nevertheless can possess aneurysm features such as dilation of the vascular tissue that can be treated similarly as the detectable aneurysm. Detectable aneurysm often serves as a signal of more prevalent weakening of the other parts of the vessel. When a large portion of the blood vessel around the aneurysm is isolated, the sealing device provides for the separate treatment of the isolated portion, such as through the delivery of a therapeutic composition to the isolated region to treat the aneurysm and strengthen the surrounding vessel.

In some embodiments, the devices disclosed herein further comprise an aspiration flow path and a delivery flow path to allow the aspiration of the isolated volume and delivery of therapeutic compositions to the isolated volume. The aspiration flow path and the delivery flow path may or may not be along the same physical pathway. If the device disclosed herein provides for the delivery of a therapeutic composition to an aneurysm or other vessel condition to the isolated volume, systemic contact with the therapeutic composition and the dilution of the therapeutic composition can be significantly reduced or eliminated. In some embodiments, the approaches described herein provide treatment of an aneurysm with intravascular approach using a device to optionally aspirate blood in the isolated volume containing the aneurysm followed by the delivery of a stabilizing agent to the isolated volume containing the aneurysm, and the blood vessel in the isolated volume containing aneurysm can be thereby stabilized and/or subject to reduced further degradation of the vessel architecture supported by structural proteins, e.g. elastin and collagen. The isolated volume therefore, serves the purpose of improving the efficacy of the stabilizing agent to treat the aneurysm. In some embodiments, the aspiration step can be performed at the same time with the delivery step through different ports of the sealing device so long as the rate of aspiration is consistently approximately equal to or greater than the rate of delivery.

In embodiments of particular interest, the isolation devices comprise a sealing introducer sheath and a sealing catheter that can be delivered through a lumen of the sealing introducer. The sealing introducer sheath comprises a sealing element at or near the distal end of the sheath, such as a balloon that can be deployed to form a proximal seal relative to the sealed segment of the vessel. The sealing catheter comprises a sealing element, such as a balloon, at or near the distal end of the catheter. Deployment of the balloon of the sealing catheter can form a distal seal for the isolated segment of the vessel. The position of the sealing catheter generally can be adjusted through the relative movement of the sealing catheter relative to the sealing introducer sheath so that the size of the isolated volume is variable and can be selected during the procedure to isolate a desired volume.

The sealing introducer sheath can comprise a balloon sealing element with a corresponding isolated balloon lumen. The balloon lumen is generally connected to a port at or near the distal end of the introducer sheath. A suitable fluid delivery device can be attached to the balloon port to control the delivery of fluid for the expansion of the balloon and removal of fluid to collapse the balloon. The sealing introducer sheath generally also has a main lumen connected to an appropriate hemostatic fitting. The main lumen and fitting can provide for the delivery of the sealing catheter through the main lumen into the vasculature past the introducer sealing element. A separate port at or near the proximal end of the introducer sheath can provide for fluid exchange with respect to the main lumen of the introducer sheath. Thus, when the sealing catheter or similar device is loaded within the main lumen, the port can be used to deliver and/or withdraw fluid from the gap between the interior of the sealing introducer main lumen and the sealing catheter, which generally opens into the isolated volume of the vessel. As noted above, the sealing introducer sheath can be used separately from the sealing catheter, for example for the performance of procedures within the femoral artery with flow stopped using the sealing element of the introducer sheath.

In some embodiments, the sealing catheter can comprise a fluid exchange opening proximal to distal the sealing element to provide fluid exchange with the isolated portion of a vessel. A fluid exchange lumen can be used to provide fluid communication between the fluid exchange opening and a proximal access port, which is at or near the proximal end of the sealing catheter. The sealing element of the sealing catheter can be a balloon, and the sealing catheter then can comprise a separate balloon lumen. A balloon port at or near the proximal end of the catheter is generally connected with a fluid delivery device to provide fluid to expand the balloon of the sealing catheter and/or to remove fluid from the balloon lumen to collapse the balloon.

In embodiments of particular interest, the balloon of the sealing catheter has concave shaped distal and proximal ends, which are connected by a generally cylindrical surface. The concave ends of the balloon assist with the balloon conforming to a particular vessel wall without applying excessive pressure on the wall. In particular, the balloon can conform through distorting at the concave ends to reduce localized pressures on the wall. The balloon can similarly be formed from a compliant polymer material that assists with the distribution of forces along the vessel wall. Using the improved balloon design, the risk of damaging fragile vessel walls can be diminished. These improved balloons can be used for sealing functions independent of the introducer sheath as well as for procedures to treat other vessel conditions in addition to aneurysms.

For appropriate embodiments, a stabilization agent maybe embedded in and/or associated with a delivery composition, such as a pluronic hydrogel and/or polymeric nanoparticles. Furthermore, multiple aspiration and delivery steps can be performed to treat the vessel sequentially with different therapeutic agents including pretreatment. For example, after the aneurysm vessel is isolated and aspirated, a pretreatment agent such as a thrombolytic agent can be delivered to break up thrombus in the isolated volume containing the aneurysm. Also, a rinsing step may optionally be applied in between treatment steps to prevent unwanted cross reaction between different therapeutic agents. In some embodiments, the isolated volume containing aneurysm may be treated first with an elastin stabilization agent followed by treatment with a collagen stabilization agent. Tagging and visualization contrasting agents can be optionally added to the therapeutic composition to help monitoring the effectiveness of the treatment process. Aneurysm treatment using the devices described herein provides versatile and non-evasive treatment options. The therapeutic compositions can be administered to aneurysm in multiple doses at various time points. Different dosage form of the therapeutic compositions can also be used for each treatment process.

While the description herein focuses on aortic aneurysms, the treatment approaches described herein can be generalized to other aneurysms as well as other vessel defects and diseases based on the teachings herein. In general, connective tissue targeted with the device can be stabilized so as to be less susceptible to protein degradation that can be brought about due to any of a variety of mechanisms and/or conditions including, for example, those associated with aneurysm, atherosclerotic disease, genetic susceptibilities, blunt force injury, Marfan's syndrome, and the like.

Connective tissue is the framework upon which the other types of tissue, e.g., epithelial, muscle, and nerve tissues, may be supported. Connective tissue generally comprises individual cells not directly attached to one another and held within an extracellular matrix. The extracellular matrix, in turn, comprises compositions excreted by specific cells with specific mechanical properties, which include, for example, fibrous components such as collagen fibers and elastin fibers. Connective tissue can assume widely divergent architectures. Blood vessels generally involve connective tissue, for example, with a thin layer of endothelial cells lining the blood vessel.

At an aneurysm, blood vessels exhibit degradation of the tissue. Due to the blood pressure in the vessel, as the tissue of blood vessel weakens, the vessel generally expands at the location of weakness. The expansion further effects flow in the vicinity of the expansion. Upon further weakening of the vessel, the vessel can rupture due to the pressure in the vessel with corresponding deleterious effects. In some embodiments described herein, the blood vessel can be sculptured to more closely resemble the natural shape of the vessel along with stabilizing the tissue such that more normal function of the vessel can be expected.

The devices disclosed herein can be directed to localized delivery of therapeutic compositions to the stabilization of the elastin and collagen component of connective tissue, and in particular, blood vessels or other vessels. It should be understood that while a device can be directed in some embodiments to the stabilization of blood vessels susceptible to the formation of aneurysms, in other embodiments, other organs, other diseases and/or other conditions can be treated. In particular, the disclosed treatment agents and treatment protocols may be applicable to any animal or human connective tissue that comprises elastin and/or collagen components.

As described herein, less invasive procedures can be used to deliver chemical stabilizing agents to stabilize the tissue in the vicinity of the aneurysm. Some level of structural remolding can be performed in conjunction with the chemical stabilization. In contrast, surgical treatment of aneurysms can involve endovascular stent graft repair (placement of a tube inside the vessel) or complete replacement of the diseased aorta or other blood vessel with an artificial vascular graft. Surgical treatment of aneurysms saves thousands of lives every year and improves quality of life. However, survival rates can drop to only 50% at 10 years post-operative due to surgery-related complications or device-related problems. In addition, endovascular stents are anatomically appropriate for only 30% to 60% of AAA patients at the outset and present the risk of endoleaks and graft displacement. Moreover, open surgery for full-size graft insertion is highly invasive, limiting its use to those patients with the ability to tolerate high operative risk. Early interventions for these potentially debilitating and life-threatening vascular pathologies may be advantageous since age is one of the major risk factors associated with the current approaches to treat aneurysms. Non-evasive diagnostic procedures can be particularly advantageous to monitor the onset as well as the development and after treatment status of aneurysm. For example, U.S. patent application Ser. No. 12/355,384 to Ogle et al. entitled "Diagnostic Biomarkers for Vascular Aneurysm," (the '384 Application), incorporated herein by reference, using biomarker to diagnose vascular aneurysm can provide valuable diagnostic information prior to and after the treatment outlined herein.

Procedures and compositions for chemical stabilization treatment of aneurysms are described generally in U.S. Pat. No. 7,252,834 to Vyavahare et al. (the '834 patent), entitled "Elastin Stabilization of Connective Tissue," and U.S. Provisional Patent Application No. 61/113,881 to Isenburg et al. (the '881 Application), entitled "Compositions for Tissue Stabilization," both are incorporated herein by reference. Additionally, delivery vehicles can be used with the therapeutic composition to facilitate the delivery of the composition to treat aneurysm. Such delivery vehicles are discussed in U.S. patent application Ser. No. 12/390,156 to Isenburg et al. (the '156 Application) entitled "Treatment of Aneurysm with Application of Connective Tissue Stabilization Agent in Combination with a Delivery Vehicle," incorporated herein by references. The devices and methods herein provide in some embodiments for effective delivery of the compositions of the '834 patent and the '881 application as well as other stabilization agents and/or other treatment agents for blood vessel tissue. The devices described herein provide for the isolation of a section of blood vessel wall to include the aneurysm using a device that can adjust the isolated volume and location of the isolation using less invasive procedures through the vasculature. Thus, the proximal end of the device remains outside of the patient while the distal end of the device is inserted through the patient's vasculature to the treatment location.

The isolation of the segment of a blood vessel associated with an aortic aneurysm can be performed through femoral arteries. Furthermore, the devices can be adapted to use for the treatment of diseases other than aneurysm. In contrast with the devices described herein, a device that can deliver a treatment fluid to a selected region of a vessel without isolating the region is described in published U.S. patent application 2007/0293937A to Biggs et al., entitled "Endoluminal Medical Device for Local Delivery of Cathepsin Inhibitors, Method of Making and Treating," incorporated herein by reference. However, if treatment fluid is released within the vessel without isolating the selected portion of the blood vessel, the treatment fluid is released into the bloodstream downstream from the selected region of the vessel for a significant systemic delivery of the treatment fluid. On the other hand, U.S. patent application Ser. No. 12/173,726 to Ogle et al. (the '726 Application) entitled "Devices for the Treatment of Vascular Aneurysm," incorporated herein by references, discloses device designs that provide for continued blood flow past the isolated region based on a specific conduit or an appropriately designed opening through the structure providing the isolated treatment location with a fixed size based on the device design.

In contrast with the devices described in the '726 application, the alternative devices described herein are capable of stably isolating larger segments of the blood vessel, although the devices herein generally do not provide for maintaining flow within the vessel past the isolated region. Most aortic aneurysms occur in the section of the aorta below or downstream from the renal arteries. The arterial vasculature below the renal arteries can be blocked for reasonable periods of time without significant detrimental effects, in contrast with other portions of the arterial system that feed the brain and organs. In particular, the aorta below the renal arteries generally can be blocked for roughly 30 minutes without significant detrimental effects for most patients. Thus, the devices described herein can be particularly effective for treating relatively large isolated and selected portions of the arterial system below the renal artery.

Isolation Device and Its Components

Devices for sealing two ends of a segment of a vessel described herein generally comprise an introducer sheath and a sealing catheter. The sealing catheter can comprise an extendable element and fluid exchange opening. The extendable element of the catheter generally has a low profile delivery configuration and a deployed, extended configuration that contacts and seals against the wall of the vessel. In some embodiments, the sealing element has concave ends that facilitate good sealing against the walls of the vessel while applying modest amounts of force against the vessel wall. The introducer sheath can comprise an extendable element that is mounted at or near the distal end of the introducer sheath. The extendable element of the introducer sheath generally has a low profile delivery configuration and a deployed, extended configuration that pushes against and seals the walls of the vessel. In some embodiments, the catheter lies coaxially inside a main lumen of the introducer sheath. The gap between the main lumen of the introducer sheath and the catheter can also optionally function as a fluid exchange lumen. In the combined device, the sealing element of the introducer sheath is located at the proximal end of the sealed vessel segment and the sealing element of the catheter is at the distal end of the sealed vessel segment.

Using the catheter and introducer sheath together, the proximal and distal extendable elements of the deployed device can contact the vessel wall upstream and down stream from the selected region in the blood vessel to form the isolated volume. The relative positions of the proximal and distal extendable elements can be adjusted based on specific therapeutic needs by sliding the catheter relative to the introducer sheath. The ability to adjust the relative positions of the extendable elements provides for the selection of the desired portion of vessel to isolate for a particular patient with significant amount of versatility. The devices and corresponding processes described herein can provide treatments to inhibit and/or reverse the progression of aneurysm, prevent further weakening and dilation of the vessel wall. The devices are designed such that procedures can be carried out in a less invasive format that reduces the recovery time and risk of the procedure to the patient.

While the sealing catheter and the sealing introducer sheath are designed for particularly effective use together for the isolation of two ends of a vessel, the devices can also be effectively used separately for appropriate procedures. For example, the catheter with its improved balloon design can be used to seal a vessel, such as a blood vessel, at locations where the vessel wall may be fragile or where greater pressure against the vessel wall is unneeded and risk of damaging the wall is particularly undesirable. Also, the sealing introducer sheath can be effectively used separately, for example to isolate portions of the femoral artery near an entry point into the vessel. In some embodiments, the femoral artery can be sealed to provide for procedures in the lower portion of the artery.

The fluid inside the isolated volume can be aspirated through the open portion of a central lumen of the introducer sheath around the exterior of the catheter. The fluid exchange opening of the catheter can provide a conduit for the delivery of a liquid, such as a therapeutic composition and/or visualization agent, to the isolated volume or for the aspiration of fluid from the isolated region. When the device is used to treat an appropriate aortic aneurysm, the extendable element of the introducer sheath can be placed inside femoral artery of one of the legs to provide the first point of sealing. The extendable element of the catheter of the device can be placed beyond the aneurysm and below the renal arteries to provide the second point of sealing. The aorta can be sealed below the renal arteries for a reasonable period of time without significant adverse effects to the patient. Additionally or alternatively, the extendable element of another introducer sheath or another sealing element can be placed inside the femoral artery of the other leg to provide the third point of the sealing. The volume inside the Y shaped vascular segment involving the aortic artery and two femoral arteries are thus isolated by the three strategically placed extendable elements as sealing points. The corresponding isolated volume can provide for effective treatment of the extent of tissue most significantly associated with the aortic aneurysm.

The extendable element or elements of the device can be balloons or the like, or using self-extending structures that achieve a desired configuration upon release within the vessel. Balloon-based devices generally comprise a lumen to deliver a liquid to inflate one or more balloons. The same lumen may or may not be used to deliver the therapeutic agent, although the use of a separate balloon lumen to control inflation of the sealing balloon provides corresponding versatility. A separate lumen such as a central lumen of the introducer sheath can be used to exchange fluid with the isolated region of the vessel. In some embodiments, the balloon of the catheter of the device is inflated with an inert liquid through a first lumen, and fluid exchange is performed through a second lumen.

In some embodiments, an extendable element can comprises self-extending elements operably connected to a suitable membrane. The self-extending elements can be released from a sheath or using an actuation tool that releases a constraint on the self-expanding element. For example, a spring metal frame can resume an extended configuration upon release from a delivery sheath. When deployed, the self-extending elements generally extend to the walls of the vessel to seal the vessel with the membrane and the self-extending element. The membrane can be a non-porous polymer membrane supported by the self extending frame.

The adjustable nature of the device with the catheter deployed through the introducer sheath provides for the ability to select within reasonable boundaries a section of the vessel to be sealed for a particular patient. The section of vessel wall associated with the enclosed volume generally includes a selected portion of the vessel wall for treatment, such as at least a portion of the aneurysm. One or more fluid exchange openings of the device provides for access to the isolated volume. In relevant embodiments, the aneurysm generally can be first identified using appropriate imaging techniques. The device can be introduced into the vessel using hemostatic techniques for the delivery of catheters and the like using less invasive procedures. The isolated volume provides for the performance of treatment on an aneurysm without exposing the treatment compositions systemically. Furthermore, the isolated volume allows the localized decrease of pressure at the aneurysm.

The distal extendable element of the device can be positioned near an aneurysm or other location for treatment within a vessel. In general, the device comprises an introducer sheath and a catheter that have extendable elements and fluid exchange lumen(s) that provide fluid exchange between the isolated volume and proximal ports that are placed outside the blood vessel. The relative positions of the extendable elements can be adjusted to selectively isolate a portion of the vessel against the wall of the vessel such that the aneurysm or other region of interest can be accessed, such as for localized delivery of a treatment fluid. The introducer sheath and the catheter of the device optionally can adopt a coaxial configuration with the catheter resides coaxially inside a central lumen of the introducer sheath. The introducer sheath may alternatively have other fitting element to allow its association with the catheter. For example, the introducer sheath may have a proximal element with branch arms having a Luer fitting or the like to provide for hemostatic access. A syringe or other fluid exchange device can be connected to the Luer fitting as desired.

Regardless of the association made, the introducer sheath and the catheter maintain the freedom for the introducer sheath to move relative to the catheter. While the device can be effective for the treatment of an aneurysm, the device can be used in other circumstances for the localized treatment of a portion of a blood vessel.

The introducer sheath can have appropriate dimensions for delivery into the patient's blood vessels. In particular, the diameter of the introducer sheath should be small enough to pass reasonably into desired vessels. The length of the shaft of the introducer sheath can have a length no more than about 50 centimeters, in some embodiments no more than about 40 centimeters, in other embodiments from about 10 centimeters to about 35 centimeters, and in further embodiments from about 12 to about 30 centimeters. The introducer sheath comprises a main lumen extending from the proximal end to the distal end of the sheath. In some embodiments, the main lumen has a diameter perpendicular to the axis of the lumen that is at least about 1.0 millimeters and no more than about 10 millimeters, in some embodiments at least about 2.5 millimeters and no more than about 7 millimeters and in further embodiments at least about 3.0 millimeters and no more than about 5 millimeters at each point along the lumen. A person of ordinary skill in the art will recognize that additional ranges of dimensions within the explicit ranges above are contemplated and are within the present disclosure.

The extendable element of the introducer sheath can comprise a sealing balloon attached on distal end of the shaft to form a balloon interior. The sealing balloon comprises a compliant polymer in an approximately cylindrically symmetrical placement around the distal end of the shaft. The sealing balloon of the introducer sheath can be transformable between a lower profile un-inflated configuration and an expanded inflated configuration. A balloon lumen can extend between the balloon interior and a port at or near the proximal end of the catheter providing fluid communication between the balloon interior and the balloon lumen. The balloon lumen can extend to a fitting, such as a Luer fitting at or near the proximal end of the introducer that provides for the attachment of a fluid source that can deliver a fluid into the balloon lumen to inflate the sealing balloon or remove fluid to subsequently deflate the balloon. The sealing balloon of the introducer sheath can have a length from about 1 millimeter to about 40 millimeters, in some embodiments from about 2 millimeter to about 30 millimeter, and in further embodiments from about 3 millimeters to about 25 millimeters. The sealing balloon can have an unrestrained expanded diameter from about 1 millimeter to about 40 millimeter, in some embodiments from about 2 millimeter to about 35 millimeter, and in further embodiments from about 5 millimeters to about 30 millimeters. The dimension of the balloon outlined above may change once the balloon is deployed inside the vessel and subject to outside pressure. A person of ordinary skill in the art will recognize that additional ranges of dimensions within the explicit ranges above are contemplated and are within the present disclosure.

The catheter can be designed to reach desired locations while maintaining an appropriate portion of the catheter extending from the patient. In general, the catheter can have a balloon lumen used to extend a balloon or the like to extend the sealing element, a second flow lumen can be used to deliver the therapeutic composition through a fluid exchange port. If the catheter has a self extending sealing element, rather than a balloon type structure, then a lumen to provide fluid to extend a balloon or the like may not be needed. In some embodiments, the catheter is designed to have appropriate dimensions for delivery through the main lumen of the introducer sheath or other appropriate fittings to the patient's blood vessels. In particular, the diameter of the catheter should be small enough to pass reasonably into the central lumen of the introducer sheath. The length of the catheter can have a length at least about 50 centimeters, in some embodiments at least about 60 centimeters, in additional embodiments from about 65 centimeters to about 125 centimeters, and in further embodiments from about 70 centimeters to about 110 centimeters. The other diameter of the catheter can be no more than about 30 millimeters, in some embodiments from about 3 millimeters to about 28 millimeters, in additionally embodiments from about 5 millimeters to about 25 millimeters. A person of ordinary skill in the art will recognize that additional ranges of dimensions within the explicit ranges above are contemplated and are within the present disclosure.

The extendable element of catheter can comprise a sealing balloon attached at or near the distal end of the catheter. The sealing balloon of the catheter can be transformable between a lower profile un-inflated configuration and an expanded inflated configuration. A balloon lumen can extend between the balloon interior and a port at or near the proximal end of the catheter, and an opening in the wall of the catheter can provide fluid communication between the balloon interior and the balloon lumen. The balloon lumen can extend to a fitting, such as a Luer fitting at or near the proximal end of the catheter that provides for the attachment of a fluid source that can deliver a fluid into the balloon lumen to inflate the sealing balloon or remove fluid to subsequently deflate the balloon.

The sealing balloon can be made from compliant polyurethane material or other suitable compliant polymer. The sealing balloon of the catheter can comprise concaved or cupped ends. The concaved or cupped ends allow the sealing balloon to be flexible while maintain tight seal against a vessel wall. The flexible sealing balloon design is aimed to reduce or eliminate any trauma the sealing balloon may have on the vessel that it is sealed. In general, the concave sealing balloon can have a length from about 5 millimeter to about 55 millimeter, in some embodiments from about 8 millimeter to 50 millimeter, and in additional embodiments from about 10 millimeter to 45 millimeter. The sealing balloon can have an unrestrained expanded diameter from about 5 millimeter to about 50 millimeter, in some embodiments from about 10 millimeter to about 48 millimeter, and in additional embodiments from about 12 millimeter to about 45 millimeter. The dimension of the balloon outlined above may change once the balloon is deployed inside the vessel and subject to pressure from its local environment. A person of ordinary skill in the art will recognize that additional ranges of dimensions within the explicit ranges above are contemplated and are within the present disclosure.

The proximal and distal concaved ends of the sealing balloon of the catheter may be of same size and shape or of different size and shape. In general, the volume of the concaved end, which can be evaluated using a planar surface to close the end, each may have a volume of about 5% to about 35%, in some embodiments about 8% to about 25%, and in further embodiments from about 10% to about 20% relative to the balloon with planar ends rather than the concave ends. The dimension of the concaved ends outlined above may change once the balloon is deployed inside the vessel and subject to outside pressure. The concave ends can have any reasonable desired shape, such as hemispheres, conical shapes or a non-specific geometrical shape. A person of ordinary skill in the art will recognize that additional ranges of dimensions within the explicit ranges above are contemplated and are within the present disclosure.

Figure 2:
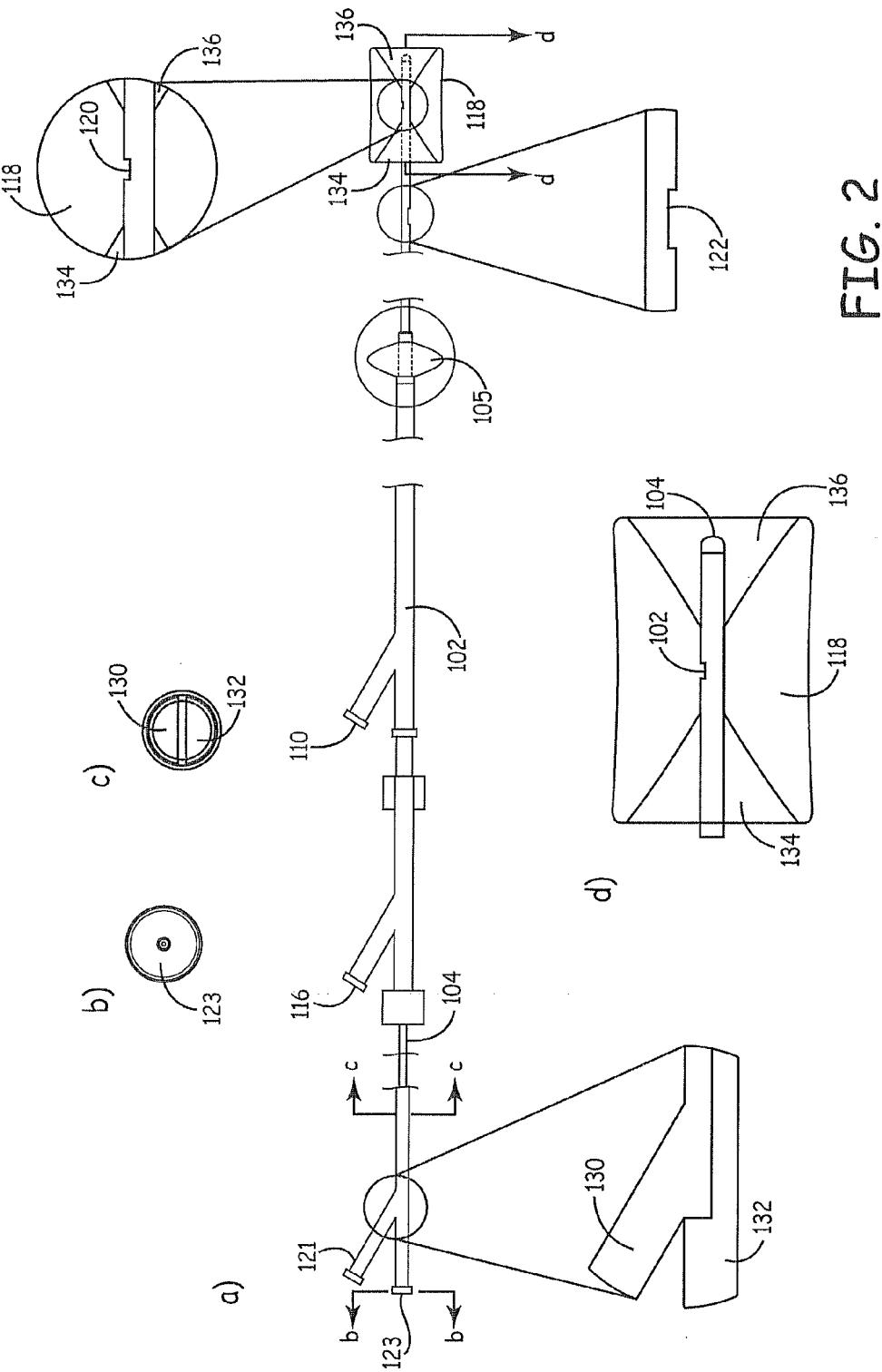
FIG. 2 is (a) a schematic side view of the sealing device with enlarged view of three major components of the sealing catheter, (b) a cross-sectional view of the port of the sealing device, (c) a cross-sectional view of the sealing catheter of the sealing device, and (d) a fragmentary cross-sectional view of the balloon of the sealing catheter with the section taken along the axis of the catheter.

Referring to FIG. 1a, a fragmentary side view of a medical device 100 with an enlarged view of a portion of the device shown in the insert. The device comprises an introducer sheath 102 and a catheter 104. Introducer sheath 102 comprises a balloon 105 near the distal end of the sheath. A radiopaque marker band 106 can be used to assist with visualization of the position of balloon 105. The interior of balloon 105 is in fluid communication with a balloon lumen 108. As shown in FIG. 1c, balloon lumen 108 is formed from the space between concentric tubular elements, but in other embodiments, other structures of the balloon lumen can be used, such as a section of the main lumen sealed off to form the balloon lumen. The balloon lumen 108 is in fluid communication with a side port 110 of the sheath 102. As shown in FIGS. 1 and 2, catheter 104 extends through a main lumen 112 of the sheath 102. Main lumen 112 is connected to and in fluid communication with a side port 116 of the sheath 102. Side port 110 and side port 116 have fittings 111 and 113, respectively, such as Luer fittings, to provide hemostatic connections to a fluid exchange element, such as a syringe, a peristaltic pump, another type of pump or the like. In particular, fitting 111 can be connected with a device to provide a biocompatible fluid, such as buffered saline to inflate balloon 105, when desired, and the device can be similarly used to deflate the balloon to facilitate removal of introducer sheath 102 at the end of the procedure.

Sealing catheter 104 comprises a balloon 118, a fluid exchange opening 122 in fluid communication with a balloon lumen and a fluid exchange lumen described further below, a side port 121 and a proximal port 123. Balloon 118 resides near the distal end of catheter 104. FIG. 1a shows balloons 105 and 118 in a lower profile un-inflated delivery configuration. FIG. 1b shows the balloon 105 when it is in the deployed or inflated configuration. The deployed or inflated configuration of the balloon 118 is shown in FIG. 2.

Referring to FIG. 2a, a schematic side view of delivery device 100 in the deployed configuration with enlarged view of three major components of catheter 104 is shown. Additionally, crossing sectional views of port 123 and lumens of catheter 104 are shown in FIGS. 2b and 2c, respectively. Catheter 104 comprises a distal balloon 118 and a distal fluid exchange opening 122 that is proximal to the distal balloon 118. The distal balloon can be inflated through an opening 120 that is in fluid communication with a balloon lumen 130 (shown in FIG. 2c) of the catheter. Balloon lumen 130 is in turn connected to and in fluid communication with side port 121. The distal fluid exchange opening 122 is in fluid communication with a fluid exchange lumen 132 (shown in FIG. 2c) of the catheter. Fluid exchange lumen 132 is in turn connected to and in fluid communication with proximal port 123. FIG. 2b shows the end view of port 123 with a liquid tight fitting, such as a Luer fitting, that can be connected to a delivery device, such as a liquid filled syringe. The convergent section of port 121 and port 123 are enlarged to show how the ports can be connected to the different lumens 130 and 132 of the catheter, respectively.

As shown in FIG. 2d, catheter balloon 118 when inflated has a general cylindrical shape along its most extended surface that has concaved or cupped ends 134 and 136. The special shape of balloon 118 is designed to provide tight and flexible contact against the vessel walls when inflated. This is particularly beneficial when treating aneurysm in major arteries where pulsation of the artery wall may make the tight seal between the deployed balloon and the vessel walls difficult while the vessel walls may be also fragile due to degradation of the vessel tissue.

The particular device in FIGS. 1 and 2 have specific designs of the lumen and the fittings. In particular, the fittings can be attached to proximal sections that are attached with fluid tight seals to the tubular sections with the lumen in fluid communication with the ports as described above and with appropriate fluid tight seals maintaining the lumen separated from each other. In other embodiments, the lumen and fittings can be formed with other designs based on the known skill in the art to equivalent functionality.

To provide for visualization of the device within the patient, the device or selected portions thereof can be formed from a radiopaque material that can be visualized using imaging techniques, such as x-ray imaging. Generally, it can be desirable to include specific imaging markers at or around the sealing element since the placement of the sealing element is directed to the isolation of a selected volume. Thus, marker bands, radiopaque components or the like can be placed at or in the vicinity of the sealing elements to assist with placement of the sealing elements at the desired location within a vessel of the body. For example, another radiopaque marker band can be placed at the distal tip of catheter 104. Also, to assist with visualization, contrast die can be included in the composition used to inflate the balloons, such that the inflated balloons can be visualized with x-ray imaging.

The device can be formed from one or more biocompatible materials, including, for example, metals, such as stainless steel or alloys, e.g., Nitinol®, or polymers such as polyetheramide block co-polymer (PEBAX®), nylon (polyamides), polyolefins, polytetrafluoroethylene, polyesters, polyurethanes, polycarbonates or other suitable biocompatible polymers. Radio-opacity can be achieved with the addition of markers, such as platinum-iridium or platinum-tungsten or through radio-pacifiers, such as barium sulfate, bismuth trioxide, bismuth subcarbonate, powdered tungsten, powdered tantalum or the like, added to the polymer resin. Generally, different sections of the device can be formed from different materials from other sections, and sections of the device can comprise a plurality of materials at different locations and/or at a particular location. Balloons and the like can be formed from suitable elastic polymers and the like.

Procedure for Isolating a Volume and Providing Localized Treatment

The devices described herein are suitable for less invasive procedures involving the isolation of a selected segment of a vessel and the performance of a procedure within the isolated region. In particular, the devices can be used in a percutaneous procedure to access blood vessels to provide treatment to the blood vessels. The sealing introducer sheath can be effective to seal the femoral artery near an entry point into the artery. The sealing catheter can be delivered to seal a selected artery at a desired location. In combination, a sealing introducer with a sealing catheter extending through the introducer can be used to form an isolated segment of vessel with appropriate sealing balloons at the sealed ends of the segment. A second sealing introducer or other sealing device can be used to seal the other femoral artery for further control of the isolated region of the arterial system including a section of the aorta branching into the two femoral arteries. The devices, for example, can be effective for procedures to treat aortic aneurysms that occur within the aorta below the renal arteries as well as other vascular diseases.

In general, using the sealing introducer sheath with the sealing catheter, the procedure overall comprises sealing the vessel and performing a procedure within the sealed segment of vessel. While the device can be used for other procedures, the discussion below focuses on the treatment of an aneurysm since the treatment of aneurysms is an issue of very significant clinical concern, and useful treatment agents have recently been developed. However, other vessel diseases or damage can be treated through the formation of an isolated volume. For example, a calcified portion of a vessel can be treated through the delivery of a thrombolytic agent, such as tissue plasminogen activator (tPA) or urokinase, or a mild acid or anti-calcification enzymes such as osteopontin to resorb calcific plaque.

The sealing introducer can be introduced, for example, using conventional techniques to establish a hemostatic entrance into the artery, generally the femoral artery. The sealing catheter can be advanced through a fitting connected to the sealing introducer to place the sealing element of the catheter at a desired location. Thus, the sealing elements of the introducer and the catheter can be placed at desired locations for the isolation of a selected segment of the vessels. The sealing elements can be deployed in a selected order to establish the sealed segment of the vessel. Optionally, a second sealing introducer or other sealing element can be placed in the other femoral artery. If a second sealing introducer is used, the lumen of the second sealing introducer can be used to exchange fluids from the sealed section of the arteries or to introduce endovascular treatment devices into the sealed section of the artery system. With respect to the delivery of endovascular treatment devices, for example, an atherectomy device or an ultrasonic device can be used to break up and remove thrombus, such as with aspiration, following delivery through the second sealing introducer. Similarly, an angioplasty balloon or a stent delivery device can be introduced through the second sealing introducer to expand partially occluded sections of the vessel and/or to provide a stent to stabilize a section of the vessel lumen.

In embodiments of particular interest, the treatment of aortic aneurysms is performed using chemical treatment fluids within the isolated vessel segments. The procedures for using the vessel isolation devices generally can comprise the steps of introducing the introducer sheath with the proximal extendable element of the device into a blood vessel, placing the distal extendable element of the catheter of the device beyond the site of aneurysm, and activating the proximal and distal extendable elements to isolate the site of aneurysm between the two elements. In some embodiments, the procedure can further comprise aspirating blood from the isolated potion of the vessel including the site of aneurysm. As described further below, it can be desirable to deliver an effective amount of a therapeutic composition into the site of the aneurysm.

The ability to aspirate liquid from the isolated portion of the vessel provides capabilities with respect to performing desired treatments within the vessel. For example, the withdrawal of blood from the isolated region can reduce the pressure in the isolated portion of the vessel, which can result in a decrease of the size of the aneurysm. The aneurysm can then be stabilized in the reduced size state. Even a modest shrinking of the size of the aneurysm can be desirable with respect to vascular function. The ability to aspirate liquid from the isolated portion of the vessel also can provide for subsequent removal of a treatment liquid after a desired amount of contact with the isolated portion of the vessel. Removal of blood prior to the delivery of a treatment fluid can improve the effectiveness of the treatment fluid since the treatment fluid is diluted less, and control of the fluid volume can reduce or eliminate an increase of pressure during the delivery of the treatment fluid since the treatment fluid is not delivered against the pressure of the artery.

In some embodiments, the procedure to treat an aortic aneurysm can comprise the delivery of a treatment fluid to an isolated portion of a vessel. In general, a treatment fluid can be delivered through a port also used for aspiration and/or through a distinct port. Following the delivery of the treatment fluid, the procedure generally comprises allowing the therapeutic composition to interact with the isolated portion of the vessel with the aneurysm for a predetermined period of time. The treatment fluid can be contacted with the vessel tissue for a desired period of time, although generally there is a limit to the period of time that it is desirable to keep the vessel blocked. After contacting the vessel with the treatment fluid for the desired period of time, the procedure can comprise aspirating the isolated portion of the vessel to remove the spent therapeutic composition. In particular, the treatment fluid or a portion thereof can be removed when desired through aspiration. Similarly, a treatment fluid can be removed prior to or simultaneously with the delivery of a second treatment fluid or a rinse fluid, such as buffered saline or the like. Optionally steps that aspirate blood from around the site of aneurysm and deliver an effective amount of a therapeutic agent into the site of the aneurysm can be repeated to achieve desired effects.

In some embodiments, the aspiration and the delivery steps can be carried out simultaneous through different lumens of the device so long as the rate of aspiration is faster than the rate of fluid delivery. The therapeutic composition delivered can be the same or different compositions during different stages of the process. For example, the delivery of one therapeutic composition can comprise the delivery of an elastin stabilization composition, and the delivery of the other therapeutic composition can comprise the delivery of collagen stabilization agent, which can be sequentially delivered in a desired order. Additionally, pretreatment steps can be carried out after or in conjunction with the initial aspiration step. For example, thrombolytic composition can be delivered into the isolated portion of the vessel to rid of thrombus and to expose vessel tissue for further treatment. To identify the location for placement of the device, appropriate imaging can be performed prior to performing the procedure as well as during the procedure. After the treatment steps have been completed and the fluid composition within the sealed section of the vessel is restored to a desired composition, the operator can deactivate the device by transitioning the sealing elements to a recovery configuration. Once the sealing elements are in a recovery configuration, the operator can withdraw the device from the blood vessel.

Methods for diagnosing and identifying the degree of aneurysm expansion are available due to developments in high resolution imaging technology (CT, MRI). Various appropriate contrast agents can be used to enhance the imaging. The use of magnetic resonance and CT imaging techniques to guide procedures on aneurysms is described further in U.S. Pat. No. 6,463,317 to Kucharczyk et al., entitled "Device and Method for the Endovascular Treatment of Aneurysms," and U.S. Pat. No. 6,793,664 to Mazzocchi et al., entitled "System and Method of Minimally-Invasive Exovascular Aneurysm Treatment," both of which are incorporated herein by reference.

Additionally, using biomarker to diagnose vascular aneurysm can provide invaluable diagnostic information prior to and after the treatment outlined herein and the diagnostic biomarkers are disclosed in the '384 Application, incorporated herein by reference. Specifically, recent techniques have been developed to track the progress of the aneurysm using a blood test and/or urine test. These biomarker tests are described further in copending '384 application, incorporated herein by reference. Once the aneurysm is identified and has progressed to a stage of initiating treatment, imaging generally is used to identify the location of the aneurysm and to assess the severity of the problem and to identify an approach for the treatment procedure. A significant majority of abdominal aortic aneurysms occur in the section of the aorta below the renal arteries, i.e., below the kidneys.

Based on the identified location of the aneurysm, the procedure can be performed by directing the combined sealing device to appropriate locations to isolate the aneurysm for the delivery of a stabilization agent. A representative procedure is presented in FIGS. 3-7 based on a device similar to the device presented above in the context of FIGS. 1 and 2. Other devices with similar functionality can be used as desired. Similarly, the device appropriately sized can be used in other vessel locations to form a selected sealed section of vessel.

Figure 3:
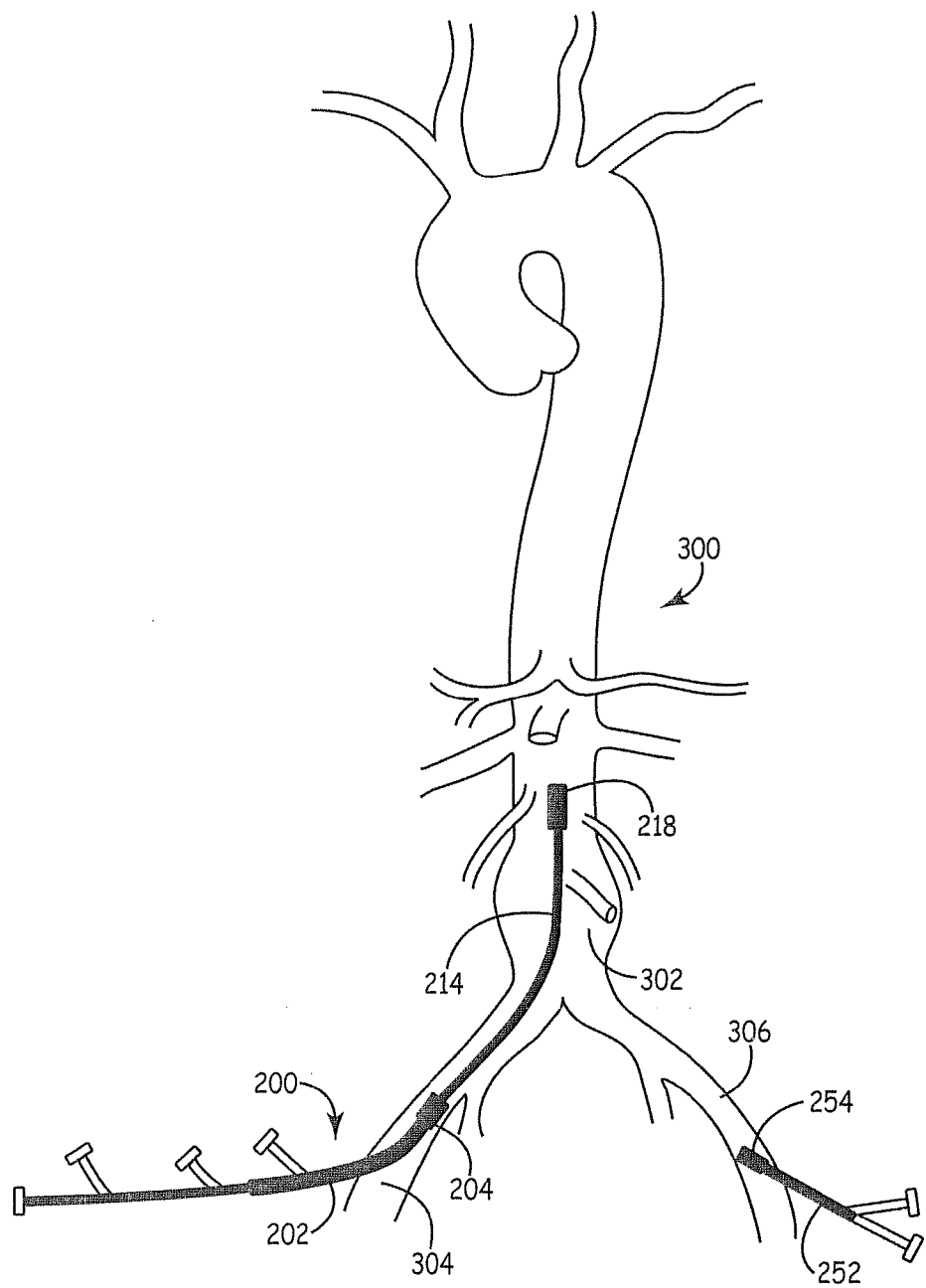
FIG. 3 is a schematic diagram of an aorta with a sealing device delivered through the femoral artery, a sealing catheter of the sealing device delivered through an sealing introducer sheath, and an extendable element of the sealing catheter delivered beyond the site of aneurysm below the renal arteries in a delivery configuration. A second sealing introducer sheath is shown delivered through the right femoral artery.

Referring to FIG. 3, distal sealing element 218 of device 200 carried on a catheter 214 is delivered into aorta 300 distal to an aneurysm 302 through an introducer sheath 202, which is introduced through the left femoral artery 304. The aneurysm 302 can be characterized by enlargement of the wall of the vessel. The distal end of the introducer sheath 202 carries a sealing element 20. Because the sealing element 204 is proximal to the aneurysm 302, it is also referred to as the proximal sealing element. Both the proximal sealing element 204 and the distal sealing element 218 are shown in a low profile delivery configuration. Radiopaque markers can be used on the device 200 to locate for example the position of sealing element 218 within the vessel during the procedure.

Another sealing element can be used in the right femoral artery 306 to seal the right femoral artery. For example, introducer sheath 252 can be introduced to the right femoral artery 306 with the distal end of the sheath carries a sealing element 254. Like the other sealing elements 204 and 218, the sealing element 254 is also in a low profile delivery configuration in FIG. 3. While introducer sheath 252 has a main lumen extending past the sealing element 254, in other embodiments a sealing balloon catheter can be used in place of introducer sheath 252 to seal the femoral artery without the fluid exchange functionality.

Figure 4:
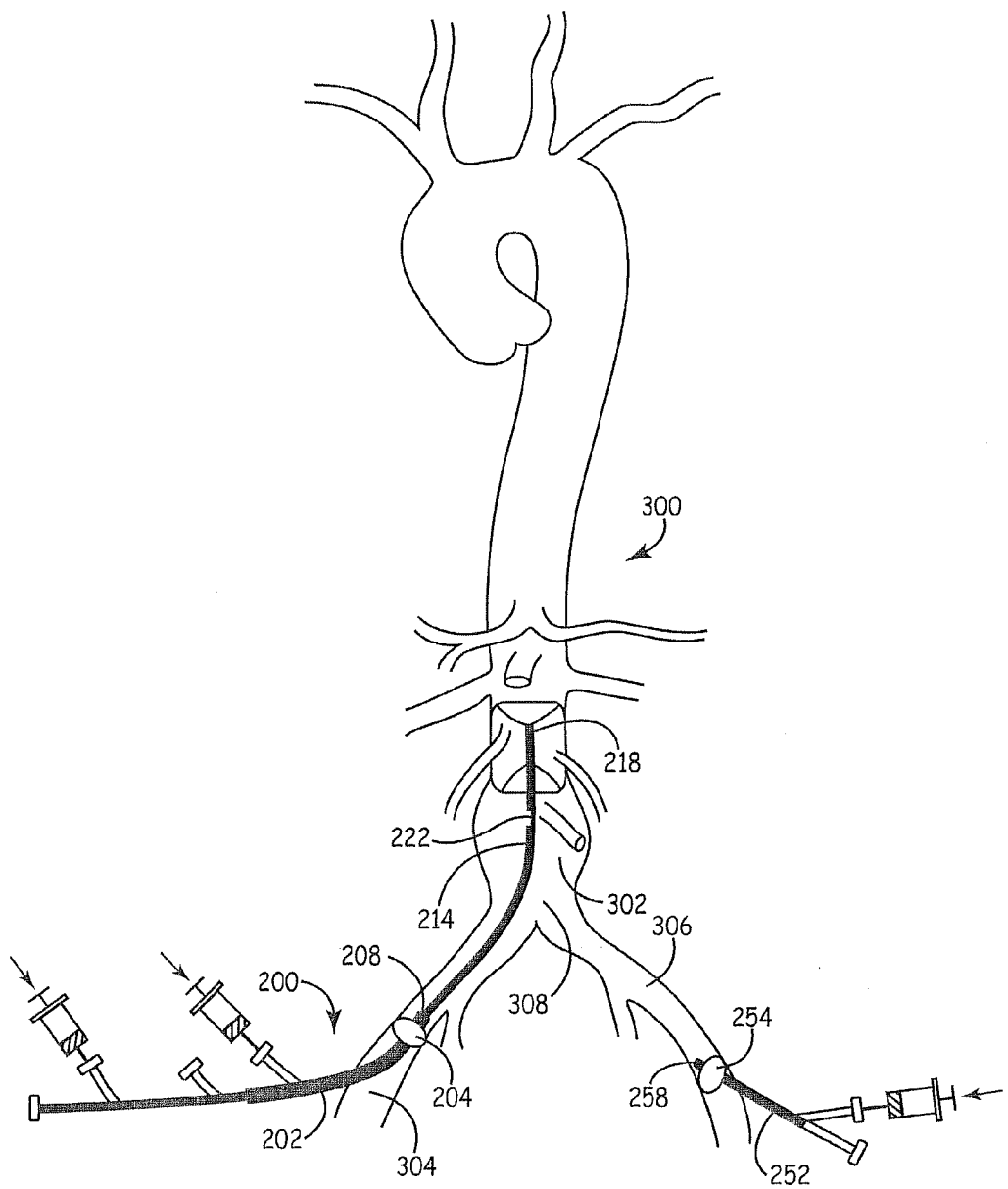
FIG. 4 is a schematic diagram of the sealing device positioned in the aorta as shown in FIG. 3, subsequent to the deployment into an extended configuration of the three extendable elements creating a "Y" shaped isolated volume.

Referring to FIG. 4, sealing elements 218, 204, and 254 are shown in extended configurations forming a "Y" shaped isolated volume 308, encompassing the aneurysm 302. The transition to the extended configuration can be performed based on the particular design of the device. For example, the transition to the extended configuration can be performed, through the filing of one or more balloons, through the release of a self extending member from a sheath or through the use of an actuation element. Fluid exchange opening 222 on the catheter 214 is configured for the exchange of fluids between a lumen of device 200 and the isolated volume 308. The gap 208 between the catheter 214 and the introducer sheath 202 can also serve as a fluid exchange lumen. Additionally, a main lumen 258 that extends through the introducer sheath 252 can also serve as a fluid exchange lumen.

Figure 5:
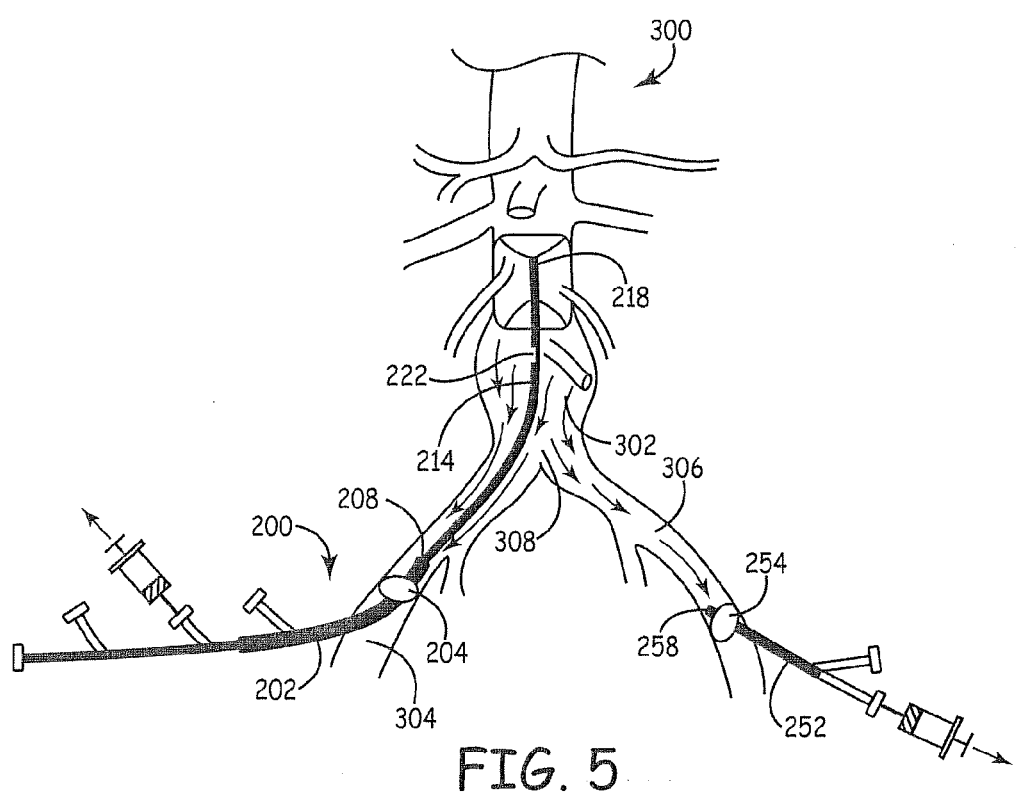
FIG. 5 is a schematic diagram of the deployed device of FIG. 4 in the aorta where the isolated volume is being aspirated.
Figure 6:
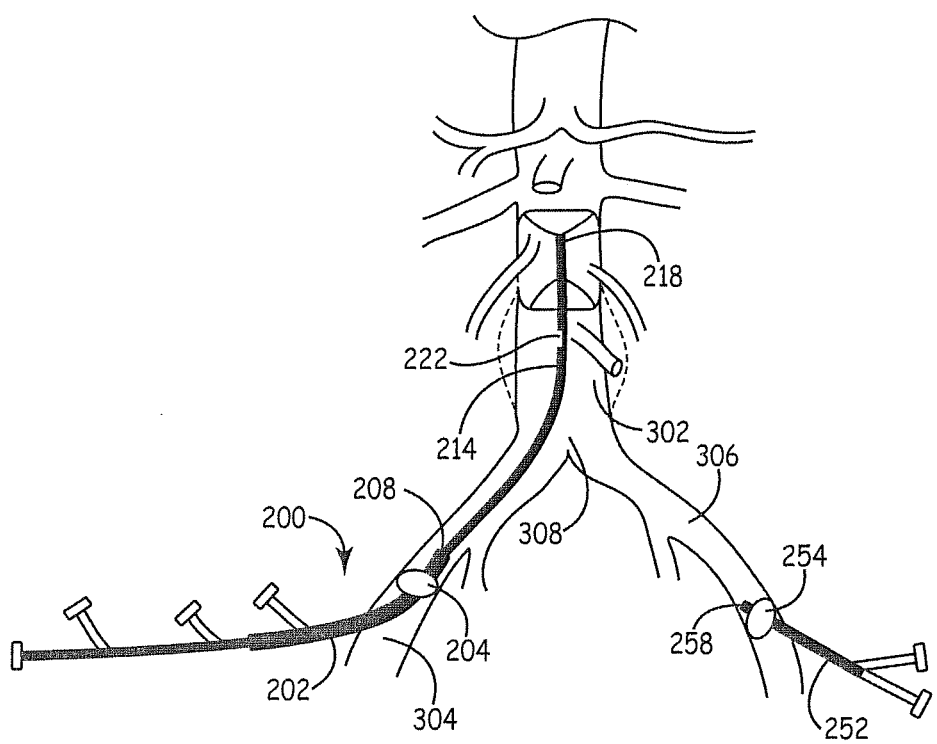
FIG. 6 is a schematic diagram of the aorta and associated vessels showing the reduced diameter of the aneurysm after the isolated volume is being aspirated according to the procedure outlined in FIGS. 3-5.

In an optional step shown in FIG. 5, blood is withdrawn from isolated volume 308 through the gap 208 and/or through the main lumen 258. The withdrawal of blood decreases the pressure in isolated volume 308, which can result in decrease or elimination of the distortion of the vessel at the aneurysm 302 as shown in the reduced diameter of the aneurysm 302 in FIG. 6.

Figure 7:
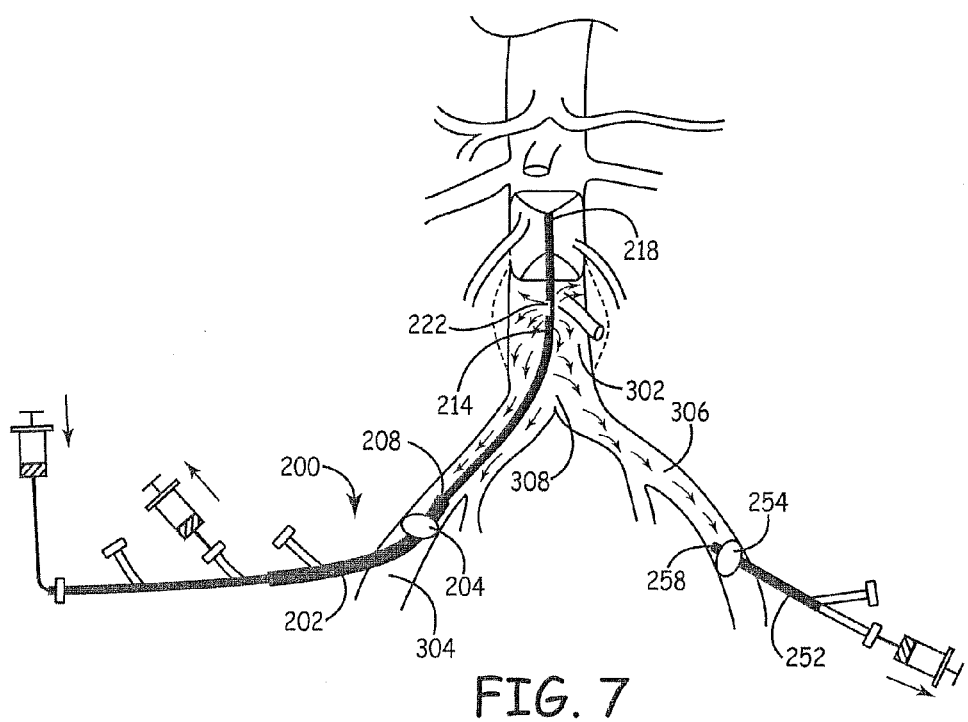
FIG. 7 is a schematic diagram of the aorta and associated vessels showing the delivery of therapeutic composition through fluid exchange openings on the sealing catheter of the device.

Referring to FIG. 7, a stabilization composition is delivered into isolated volume 308 where it can interact with aneurysm 302 to stabilize the vessel at the aneurysm. The stabilization composition can be delivered through a lumen of the catheter 214 of device 200 through fluid exchange opening 222. Aspiration maybe applied through the gap 208 and the fluid exchange lumen 258 to facilitate the delivery of the therapeutic composition through the entire isolated volume 308. Because the isolated portion of the artery does not feed directly into major organs or the brain, a reasonable period of time can be allowed for the stabilization composition to act on the vessel wall. In some embodiments, the treatment can last for a period of time from about 1 minute to about 40 minutes, in further embodiments from about 5 min. to about 35 min., and in additional embodiments from about 10 min. to about 30 min. A person of ordinary skill in the art will recognize that additional ranges of treatment times within the explicit ranges above are contemplated and are within the present disclosure. In general, with respect to FIGS. 3-7, aspiration and fluid delivery have been discussed in the context of particular ports. However, in general any lumen in fluid communication with the isolated region of the vessel and a port outside of the patient can be used to aspirate and/or deliver a fluid at a selected time in the procedure. Therefore, the particular lumen described in the figures above can serve other fluid exchange functions.

With respect to embodiments in which the aspirating step and/or the delivering of the therapeutic composition steps are repeated at least once and in which the therapeutic compositions delivered can be the same or different compositions, the treatment times discussed herein for the repeated steps can be the same or different. For example, the delivery of one therapeutic composition can comprise the delivery of collagen stabilization agent, which is allowed to act on the vessel for example, from about 2 min to about 2.5 hours, in further embodiments from about 5 min. to about 2.25 hours, and in additional embodiments from about 10 minutes to about 2.0 hours. The delivery of the other therapeutic composition comprises the delivery of an elastin stabilization composition which is allowed to act on the vessel, for example, from about 5 minutes to about 2.5 hours, in some embodiments about 15 min. to about 2.25 hours and in further embodiments from about 30 minutes to about 2.0 hours. In some embodiments, the portions of the procedure with an occluded vessel can take a period of no more than about 4 hours, in additional embodiments from about 5 minutes to about 3.5 hours, and in further embodiments from about 15 minutes to about 3 hours. A person of ordinary skill in the art will recognize that additional ranges of time within the explicit ranges above are contemplated and are within the present disclosure. Once the selected period of time has passed for providing contact with the stabilization composition, the isolated volume 308 can be optionally aspirated, using similar process as described in FIG. 5. The aspirated isolated volume may optionally be filled with fluid such as blood that was aspirated at the beginning of the procedure. The blood maybe treated before being returned to the vessel, such as filtration or addition of anti-coagulant.

The sealing element can subsequently be transitioned to a recovery configuration, which can approximate the delivery configuration, with a lower profile and without fondling an isolated volume. The transition to the recovery configuration can comprise, for example, the deflation of one or more balloons, the folding of a compliant frame using a sheath or the like, or the use of an actuating member to transition the extendable element. Once the sealing element is transitioned to the recovery configuration, device 200 or the introducer sheath 252 can be removed from the patient.

In general, the procedure outlined in FIGS. 3-7 can be performed with alternative embodiments discussed herein. In some embodiments, additional steps of delivering and removing liquids from the isolated region can be performed if desired, such as for the sequential contact with stabilization fluids. In one embodiment, the step of delivering the therapeutic composition is repeated with a different composition, wherein the delivery of one therapeutic composition comprises the delivery of an elastin stabilization composition and the delivery of the other therapeutic composition comprises the delivery of collagen stabilization composition.

As noted above, the components of the combined sealing devices can be separately used in appropriate procedures. For example, the sealing introducer can be used to seal the femoral artery for the treatment of the distal portions of the femoral artery. In these embodiments, the introducer can be placed with the distal end of the introducer pointed downstream into the particular femoral artery. When the seal is deployed, a procedure can be performed in the sealed artery, which may or may not involve the delivery or removal of fluid from the sealed portion of the artery.

Similarly, the sealing catheter can be used to seal a selected location within an artery. The concave design of the balloon provides for good sealing with a significant amount of force against the vessel wall while applying less pressure, i.e. force per unit area, on the vessel wall so that the sealing catheter can be effectively used for fragile vessels where excessive pressure is contraindicated. In some embodiments, the balloon has a significant amount of surface area. Desired procedures can be performed in the vessel with the seal in place. The seal can be used, for example, to diminish migration of emboli from the treatment location. For example, the sealing catheter can be used in carotid arteries or in the aorta to provide temporary blockage of flow while performing procedures in the artery.

Treatment of the isolated volume with therapeutic compositions can be combined with mechanical stabilization. In particular, a perivascular girdle wrap can be placed over the exterior of the aneurysm to provide mechanical stabilization along with the chemical stabilization. The girdle wrap physically strengthens the vasculature at the aneurysm site to prevent it from bursting while the stabilizing agents can act to stabilize and strengthen the tissue of the vessel along with inhibiting further degradation of the vessel at the location of the aneurysm. The wrap can be formed from biocompatible polymers, such as polyesters, that can be formed into woven or non-woven fabrics.

Therapeutic Composition—Formulation and Delivery Options

Therapeutic compositions can be delivered to the isolated region of the blood vessel to provide beneficial effects on the vessel. For aneurysms, the therapeutic compositions can be selected to stabilize the vessel structure, for example, through the stabilization of elastin and/or collagen which are structural proteins in the blood vessel wall. In general, suitable stabilizing therapeutic compositions can be provided in pharmaceutically acceptable formulations, such as using formulation methods known to those of ordinary skill in the art. These formulations can generally be administered to connective tissue associated with an isolated volume in the vicinity of an aneurysm through the device described herein. In some embodiments, the therapeutic compositions can comprise a phenolic compound that interacts with elastin to stabilize the tissue, and in additional or alternative embodiments, the stabilization composition comprises a collagen crosslinking agent. Thus, in some embodiments, a therapeutic composition can comprise a phenolic compound, as described further below, as well as a distinct collagen crosslinking agent.

Once delivered to the targeted blood vessel by any suitable method, the composition can access and then stabilize the connective tissue of the vessel. For instance, when delivered to the connective tissue from the lumen of a blood vessel, the composition disclosed herein may penetrate the endothelium of the vessel wall to contact the elastin and/or collagen of the connective tissue and stabilize the structure architecture. The therapeutic compositions can be delivered with a delivery vehicle to provide further control of the therapeutic delivery, as described further below.

Therapeutic compositions can comprise additional agents, in addition to agents that stabilize elastin and/or collagen. Such additional agents can be active agents, providing direct benefit to the tissue, or may be supporting agents, improving imaging, delivery, compatibility, or reactivity of other agents in the composition. For example, the composition can incorporate a gallic acid scavenger, for example ascorbic acid or glutathione, so as to decrease or prevent the release of free gallic acid residues. Also, the therapeutic composition can be combined with any of a number of possible lipid-lowering medications so as to prevent the development of calcified lipid deposits or arteriosclerosis plaques that can often be found in conjunction with aneurysm formation.

The therapeutic compositions can comprise additional agents in some embodiments in a concentration from about 0.0001% to about 10% by weight. For example, a particular selected concentrations of an additional agent may be influenced by the size of the targeted area, desired incubation time, and selected pH. In one embodiment, the disclosed compositions can comprise concentrations of the additional agent ranging from about 0.01% to about 2% by weight and in additional embodiments from about 0.1% to about 1% by weight. A person of ordinary skill in the art will recognize that additional ranges within the explicit ranges above are contemplated and are within the present disclosure.

The therapeutic composition can comprise one or more buffers. For example, a composition having a pH from about 4.0 to about 9.0 may be formulated with inclusion of purified water, saline and a biocompatible buffer, such as phosphate buffers, borate buffers, HEPES, PIPES, MOPSO or combinations thereof. In one embodiment, a composition of the invention may be formulated to have a pH of between about 5.5 and about 7.4. Therapeutic compositions can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (e.g., glycerol, propylene glycol, polyethylene glycol and the like), carboxymethylcellulose and suitable mixtures thereof, vegetable oils (e.g., olive oil) and injectable organic esters such as ethyl oleate. In addition, the composition can contain minor amounts of auxiliary substances such as wetting or emulsifying agents, pH buffering agents and the like that can enhance the effectiveness of the vessel stabilizing compound. Proper fluidity may be maintained, for example, by the use of coating materials such as lecithin, by the maintenance of the required particle size in the case of dispersions and by the use of surfactants. These compositions may also contain adjuvants such as preservatives, wetting agents, emulsifying agents and dispersing agents. The therapeutic compositions should be appropriately sterile at the time of use.

Prevention of the action of microorganisms may be ensured by the inclusion of various antibacterial and antifungal agents such as paraben, chlorobutanol, phenol, sorbic acid and the like. It may also be desirable to include isotonic agents such as sugars, sodium chloride and the like.

In some embodiments, the compositions can include pharmaceutically acceptable salts of the components therein, e.g., those that may be derived from inorganic or organic acids. Pharmaceutically acceptable salts are well known in the art. For example, S. M. Berge, et al. describes pharmaceutically acceptable salts in detail in *J. Pharmaceutical Sciences*

(1977) 66:1 et seq., which is incorporated herein by reference. As noted above, a suitable rinsing composition to facilitate removal of therapeutic compositions would comprise buffered saline, such as buffered sodium chloride.

For monitoring and/or research purposes, the therapeutic composition can further comprise a tag, a contrast agent, or a combination thereof. For example, the therapeutic composition can be tagged with radioactive atoms such as tritium.

Elastin and Collagen Degeneration within Aneurysms

Elastin and collagen are protein constituents of connective tissue contributing to the structural integrity of the tissue. Moreover, elastin and collagen are quite abundant in connective tissue. For example, elastin is considered the most abundant extracellular matrix protein found in the aortic wall. Elastin polypeptide chains are naturally cross-linked together to form elastic fibers. Elastin molecules can uncoil into a more extended conformation when the fiber is stretched and will recoil spontaneously as soon as the stretching force is relaxed. Elastin degeneration in connective tissue pathology is generally believed to be caused by enzymes including elastase enzymes and matrix metalloproteinase (MMP) enzymes that can be secreted by vascular cells as well as by infiltrating inflammatory cells. While many aspects of the methods and schemes of various enzymes leading to elastin degradation remain unknown, in general, it is believed that most enzymes attack and bind the protein at a site away from the natural crosslinks.

The characteristics of aneurysms are degeneration of arterial structural proteins including elastin and collagen, inflammatory infiltrates, calcification, and overall degeneration of arterial architecture. This results in loss of mechanical properties and progressive dilatation. Due to its insolubility, natural desmosine and isodemosine crosslinks, and extremely long biological half-life, elastin is generally perceived to be resistant to degradation. However, there is a specific set of enzymes, matrix metalloproteinases (particularly MMP-2, MMP-9, and MMP-12), which are capable of degrading elastin. MMPs are involved in normal physiological processes such as bone remodeling, wound healing, and angiogenesis. However, abnormally high levels of MMPs have been identified in pathological processes in many vascular diseases, and appear to be significant contributors to the formation and progression of AAAs. This identification is underlined by consistent reports of severe elastin degradation within aneurysmal tissues, as evidenced by heavy degeneration of the arterial architecture, decreased medial elastin content, and disrupted or fragmented elastic lamellae. This degradation is particularly significant when one considers the inability of elastin to promptly revitalize itself (as evidenced by its nearly 70-year biological half-life), unlike some other relatively dynamic matrix components.

Furthermore, degradation of elastin results in the release of soluble elastin peptides. These peptides are not passive by-products of the degradation process; rather, it has been demonstrated that they are active in protease production, chemotaxis, cellular proliferation, and various other biological activities. The release of elastin peptides can result in a cascade of even more matrix degradation, as it has been suggested that interactions between these peptides and smooth muscle cells increase expression of the elastin laminin receptor (ELR). This binding with ELR, a 67 kDa receptor found on a number of cell types, subsequently results in the promotion of greater MMP synthesis both at the mRNA and protein levels. Numerous studies have supported this correlation between up regulated MMP activity and the presence of elastin peptides. The use of luminally-perfused elastin peptides within an aneurysm animal model, which elicits elevated MMP levels and matrix degradation at the site of perfusion, also supports the biological significance of these peptides. The bioactivity of elastin peptides underscores the clinical significance of elastin degradation within aneurysmal tissues and the desire to protect elastin from degeneration.

It is believed that any of a number of natural and synthetic phenolic compounds can bind elastin and thereby protect elastin from degradation, for instance due to the action of elastin degrading enzymes. Accordingly, in one embodiment, devices described herein and corresponding methods can be effectively used to deliver compositions that can inhibit enzyme-catalyzed degradation of elastin, and in particular elastase and/or MMP catalyzed degradation of elastin.

Additionally, at an aneurysm, collagen is present throughout the connective tissue. In the course of aneurysm development, it has been suggested that the processes of degradation and regeneration of collagen alternates. Once the collagen degradation reaches a particular degree, the rupture of the aneurysm tissue may occur. See, for example, Choke E, Cockerill G, Wilson W R, et al. *Eur J Vasc Endovasc Surg* 2005; 30(3): 227-244, incorporated herein by reference. Stabilization of collagen in aneurysm tissue can be an effective aspect for treating vessel damage associated with an aneurysm.

Collagen crosslinking/stabilization agent can provide a significant degree of stabilization of vascular tissue associated with aneurysms and other degeneration of blood vessels. The treatment agents can be contacted with the tissue simultaneously or sequentially. Multi-functional reagents, such as glutaraldehyde, genipin, acyl azide, and epoxyamine, are known to cross-link functional groups in collagen thereby stabilize collagen and tissue having a collagen component. These collagen crosslinking/stabilization agents can be incorporated into a therapeutic composition to stabilize tissues associated with an aneurysm or the like. The therapeutic composition can further comprise an elastin stabilizing agent, or a plurality of therapeutic compositions can be delivered sequentially or simultaneously to effectuate elastin stabilization and collagen stabilization. The combination of an effective collagen crosslinking/stabilization agent and an elastin stabilization agent are effective with respect to stabilizing vascular tissue, such as an aneurysm tissue. In general, connective tissue targeted with the therapeutic agent(s) or composition(s) can be stabilized so as to be less susceptible to protein degradation as well as having improved mechanical strength to resist distortion of the natural shape and possible bursting. The degradation of the tissue can be brought about due to any of a variety of mechanisms and/or conditions including, for example, those associated with aneurysm, atherosclerotic disease, genetic susceptibilities, blunt force injury, Marfan's syndrome, and the like.

Phenolic Compounds as Elastin Stabilization Agents

For elastin stabilization, phenolic compounds in some embodiments include any compound that includes at least one phenolic group bound to a hydrophobic core. While not wishing to be bound by any particular theory, it is believed that interaction between the phenolic compound and elastin proteins may include aspects involving both the hydroxyl group as well as the hydrophobic core of the molecules. In particular, it is believed that phenolic compounds can stabilize elastin proteins through both steric means and bond formation and thereby protect sites on the protein susceptible to enzyme-mediated (e.g., elastase or MMP-mediated) cleavage. Specifically, it is believed that hydroxyl groups of a phenolic compound can bind elastin multivalently, for instance via hydrogen bond formation with amino acid residues such as polar amino acid residues including methionine, glycine and proline, such that multiple proteins can interact with a single molecule to create a three-dimensional cross-link structure involving multiple elastin molecules. Moreover, in certain embodiments, the phenolic compounds of the present invention can comprise one or more double bonds, with which the phenolic compounds can covalently bind to the elastin, forming an even stronger and more permanent protective association between the phenolic compound and the elastin of the connective tissue.

In addition, the large hydrophobic regions of the elastin protein, which are believed to contain sites susceptible to elastase-mediated cleavage, are also believed to contain sites of association between the hydrophobic core of the phenolic compound and the protein. Thus, the association between the phenolic compound and the protein molecules are believed to protect specific binding sites on the protein targeted by enzymes through the association of the protein with the hydrophobic core and may also sterically hinder the degradation of the protein through the development of the large three dimensional cross-link structures. Stabilization of connective tissue through the interaction of therapeutic agents with elastin component tissue is discussed in U.S. Pat. No. 7,252,834 to Vyavahare et al. (the '834 patent), entitled "Elastin Stabilization of Connective Tissue," incorporated herein by reference.

Phenolic compounds of particular interest include, for example, materials including a hydrophobic core and one or more phenol groups extending from the hydrophobic portion of the molecule. For instance, exemplary phenolic compounds of the invention can include, but are not limited to, flavonoids and their derivatives (e.g., anthocyanins, quercetin), flavolignans, phenolic rhizomes, flavan-3-ols including (+)-catechin and (−)-epicatechin, other tannins and derivatives thereof (such as tannic acid, pentagalloylglucose, nobotanin, epigallocatechin gallate, and gallotannins), ellagic acid, procyanidins, and the like.

Phenolic compounds encompassed herein also include synthetic and natural phenolic compounds. For example, natural phenolic compounds can include those found in extracts from natural plant-based sources such as extracts of olive oil (e.g., hydroxytyrosol (3,4-dihydroxyphenylethanol) and oleuropein, extracts of cocoa bean that can contain epicatechin and analogous compounds, extracts of *Camellia* including *C. senensis* (green tea) and *C. assaimie*, extracts of licorice, sea whip, aloe vera, chamomile, and the like.

The phenolic compounds described herein can be tannins and derivatives thereof. Tannins can be found in many plant species. For example, the tea plant (*Camellia sinensis*) has a naturally high tannin content. Green tea leaves are a major plant source of tannins, as they not only contain the tannic and gallic acid groups, but also prodelphinidin, a proanthocyanidin. Tannins are also found in wine, particularly red wine as well as in grape skins and seeds. Pomegranates also contain a diverse array of tannins, particularly hydrolysable tannins.

In general, the phenolic compounds described herein can be provided as a component of a therapeutic composition. Cytotoxicity of the agents can also be of importance in preparation of therapeutics including the disclosed compounds. At one time, tannic acid-containing preparations were suspected of causing hepatoxicity. This toxicity has since been primarily attributed to poor purity of the preparations and the inclusion of toxic gallic acid residues in the compositions. Accordingly, the compositions can include high purity tannic acid, with little or no free gallic acid residue included in the compositions. For example, the compositions can comprise no more than about 5% free gallic acid residue in the preparation.

Additionally, a therapeutic composition can comprise an effective amount of pentagalloylglucose (PGG) as an elastin stabilizing agent. The PGG molecule comprises a fragment of a tannic acid molecule, including the hydrophobic core of tannic acid as well as multiple phenolic hydroxy groups, but without the outer gallic acid residues and the hydrolyzable ester bonds associated with tannic acid. Thus, the possibility of release of free gallic acid residues over the course of a long-term application process can be prevented through utilization of a compound having no gallic acid residues, such as PGG, as the selected agent.

Compositions disclosed herein can comprise one or more phenolic compounds in a concentration that can vary over a selected range, with a concentration generally depending on the particular application, the delivery site targeted by the phenolic compound and the mode that will be used in the delivery process. For example, in some embodiments, a therapeutic composition can comprise one or more phenolic compounds at a concentration from about 0.0001% to about 10% by weight. A selected concentration used may be influenced by the vessel targeted by the procedure, size of the targeted area, desired incubation time, and preferred pH. In one embodiment, the disclosed compositions can include concentrations of a phenolic compound ranging from about 0.01% to about 2% by weight and in additional embodiments from about 0.1% to about 1% by weight. A person of ordinary skill in the art will recognize that additional ranges within the explicit ranges above are contemplated and are within the present disclosure. Use of phenolic compositions for aneurysm stabilization is described further in U.S. Pat. No. 7,252,834 to Vyavahare et al., entitled "Elastin Stabilization of Connective Tissue," incorporated herein by reference.

Collagen Stabilization Agents

Collagen stabilization agents are generally multi-functional agents that cross-link reactive groups, such as amino, thiol, hydroxyl, and carbonyl, in collagen and/or nearby proteins. By binding to and crosslinking collagen and/or nearby proteins, the multi-functional agents can increase the mechanical strength of the tissue. In the case of aneurysm, the increased mechanical strength of aneurysm vessel increases the tolerance of the treated aneurysm tissue to burst pressure, thus decrease the risk of rupture of the vessel. Some collagen stabilization agent maybe used for facile in vivo treatment employing an appropriate delivery device that can direct the therapeutic agent to the desired location. Agents may have acute in vivo toxicity such that isolation of the treatment site during the treatment process can be very advantageous. Stabilization of connective tissue through collagen as well as the elastin components of the tissue are described further in U.S. Provisional Patent Application No. 61/113,881 to Isenburg et al. (the '881 Application), entitled "Compositions for Tissue Stabilization," incorporated herein by reference.

Tissue treated with collagen crosslinking/stabilization agent with or without combination with elastin stabilization agent may exhibit enhanced mechanical properties, resistance to enzymatic degradation such as elastase and collagenase, and high thermal denaturation temperature. The thermal denaturation temperatures ($T_d$) are common indicators of collagen crosslinking density and corresponding stability, which can be measured using a differential scanning calorimeter (DSC).

Glutaraldehyde

Glutaraldehyde has been widely used for decades as an in vitro tissue fixative for bio-prosthetic heart valves due to its ability to crosslink collagen, sterilize tissue, and reduce tissue antigenicity. Other bi-functional or multi-functional aldehyde compounds can be similarly used. Glutaraldehyde and other multi-functional aldehyde compounds bind to and stabilize collagen in the wall of the vessel. In particular, glutaraldehyde self-polymerizes to form polymer chains that are believed to be effective at crosslinking between collagen fibers.

Glutaraldehyde polymerizes with itself and/or with nearby active groups from collagen and/or other proteins creating crosslinks in the treated tissue. The chemical crosslinks in the tissue can contribute to increased resistance to degradation of the treated tissue. However, residual unreacted free aldehyde groups from glutaraldehyde can contribute with regards to toxicity and calcification. Treatment of bioprosthetic tissue to reduce toxicity is described in U.S. Pat. No. 6,471,723 to Ashworth et al., entitled "Biocompatible Prosthetic Tissue," incorporated herein by reference. Similar treatment to reduce the residual unreacted free aldehyde groups in the glutaraldehyde treated isolated blood vessel maybe used to reduce toxicity of the overall treatment. By binding to and crosslinking collagen, glutaraldehyde increases the mechanical strength of the tissue. The in vivo application of the glutaraldehyde alone and in combination with PGG have been discussed in the '834 patent with respect to treatment of aneurysms. For in vivo treatment directly at the site of the aneurysm inside a blood vessel, however, the amount of glutaraldehyde, treatment concentration, treatment time, toxicity control agent etc. used can be selected to achieve desired treatment effects while avoiding undesirable effects from excessive treatment, such as excessive cellular toxicity and over-stiffening of the vessel well. Preliminary in vitro experiment results using glutaraldehyde and/or an elastin stabilizer such as PGG or tannic acid have been presented and discussed in further detail in examples 1-5 of the '834 patent.

Carbodiimides

One of the alternative collagen stabilizing agents comprises diamines, generally with at least two free primary amine groups, such as 1,6-hexanediamine and 1,7-heptanediamine. The diamines bond to carboxyl groups in proteins to form a crosslinked structure. It has been found that coupling agents and coupling enhancers facilitate this crosslinking/stabilization process with diamines. For example, suitable coupling agents include carbodiimides, such as 1-ethyl-3-(3-dimethyl aminopropyl)-carbodiimide (ECD) and/or n-hydroxysuccinimide (NHS). The carbodiimides function as a coupling agent in the crosslinking/stabilization reaction, and are generally used along with a coupling enhancer. For example, EDC can be used in conjunction with N-hydroxysulfo succinimide (Sulfo-NHS), which acts as an enhancer to the reaction. Other suitable coupling enhancers include, for example, N-Hydroxybenzotriazole (HOBO, 4-(Dimethylamino)pyridine (DMAP) and NHS. By coupling the amine and carboxyl groups within the tissue, this treatment creates amide bonds or bridges between and/or inside proteins, thus crosslinking/stabilization the tissue. In vitro crosslinking/stabilization of bioprosthetic tissue with diamines along with coupling agents and/or coupling enhancers is described further in published U.S. patent application 2006/0159641A to Girardot et al., entitled "Variably Crosslinked Tissue," incorporated herein by reference.

Photo-Oxidation

Collagen stabilization in tissue can also be triggered by a light sensitive dye, similar to the PhotoFix™ technology used by Carbomedics for bioprosthetic heart valves. Photo-oxidation fixation relies on the use of a photoactive dye as a catalyst. Suitable dyes include, for example, methylene blue, methylene green, rose bengal, riboflavin, proflavin, fluorescein, eosin, pyridoxal-5-phosphate and combinations thereof. The catalyst aids in the conversion of amino acids within the tissue, subsequently allowing for crosslink formation between the converted amino acid and nearby amino acids to stabilize the tissue, as shown for example, in the following articles: Adams A K, Talman E A, Campbell L, et al. *J Biomed Mater Res* 2001; 57(4): 582-587 and Meuris B, Phillips R, Moore M A, et al. *Artif Organs* 2003; 27(6): 537-543), both of which are incorporated by reference.

Methods for ex vivo cross-linking collagen with a photo-catalyst are described further in U.S. Pat. No. 5,147,514 to Mechanic et al, entitled "Process for cross-linking collagenous material and resulting product," incorporated herein by reference. Photo-oxidation requires exposure of the treated tissue to a light source. In the case of aneurysm treatment, such light source can be supplied by for example, optical fiber. Additionally, oxygen may need to be supplied to the therapeutic composition to facilitate the completion of the photo-oxidative reaction.

Genipin

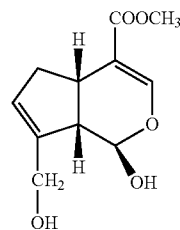 [SMILES: COC(=O)C1=CO[C@@H](O)[C@@H]2C(CO)=CC[C@H]12]

Genipin, with a formula shown above, is a naturally occurring plant compound capable of crosslinking/stabilization collagen. Stereoisomers and mixtures thereof, such as racemic synthetic genipin, can be similarly used. Similarly, functionally active derivatives thereof can also be used to crosslink collagen. Genipin is known to react with amino acids and/or proteins to form a dark blue pigment, which has been historically used as a food dye. It has been shown that genipin is a relatively non-toxic compound for collagen crosslinking/stabilization. See the description in the following articles: Sung H W, Chang Y, Chiu C T, et al. *Biomaterials* 1999; 20: 1759-1772 and Sung H W, Chang W H, Ma C Y, et al. *J Biomed Mater Res* 2003; 64A: 427-438, both of which are incorporated by reference. Methods for ex vivo cross-linking collagen for bioprosthetic tissue are described in U.S. Pat. No. 6,608,040 to Sung et al., entitled "Chemical Modification of Biomedical Materials with Genipin," incorporated herein by reference. Additionally, genipin has been used in vascular stent as a collagen crosslinking/stabilization agent for treating vulnerable plaques of a patient as described in U.S. Pat. No. 7,351,421 to Sung et al., entitled Drug-Eluting Stent Having Collagen Drug Carrier Chemically Treated with Genipin," incorporated herein by reference.

Epoxies

Epoxy compounds have reactive functional groups that are reactive with several functional groups found in proteins, and epoxies can be used to crosslink proteins, especially collagen, within tissue. For example, the use of epoxy polymers as a collagen crosslinking/stabilization agent for heart valve tissue is described in U.S. Pat. No. 5,080,670 to Imamura et al., entitled "Bioprosthetic Valve," incorporated herein by reference. The compositions described in the '670 Imamura patent include polyglycidyl ethers of polyglycerols having a polymerization degree of 1 to 3 as well as polyglycidyl ethers of polyols, and some specific examples of compositions include, for example, glycerol diglycidyl ether, glycerol triglycidyl ether, digylcerol tetraglycidyl ether and ethylene glycol glycidyl ether. Non-polymeric epoxy collagen crosslinking/stabilization agents are described in U.S. Pat. No. 5,880,242 to Hu et al., entitled "Nonpolymeric Epoxy Compounds for Cross Linking Biological Tissue and Bioprosthetic Grafts Prepared Thereby," incorporated herein by reference. This patent describes compounds with a formula $R_1$—$CH_2$—O—X—O—$CH_2$—$R_2$, where X is a straight chain aliphatic hydrocarbon with either 4 or 5 carbon atoms, $R_1$ or $R_2$ or both are epoxy groups, and the other of $R_1$ or $R_2$ is an aldehyde group if it is not an epoxy group. A specific example of a nonpolymeric epoxy crosslinking/stabilization compound is 1,4-butanediol diglycidyl ether.

Epoxy amine polymer compounds are also suitable collagen crosslinking/stabilization agents. The use of these compounds as tissue, i.e., collagen, crosslinking/stabilization agents is described further in U.S. Pat. No. 6,391,538 to Vyavahare et al., entitled "Stabilization of Implantable Bioprosthetic Tissue," incorporated herein by reference. An example of a suitable poly-epoxyamine compound suitable as a collagen crosslinking/stabilization agent is triglycidylamine, a triepoxy amine.

Triglycidylamine (TGA) is a highly polar, water soluble, polyepoxy-crosslinking agent. TGA appears to bind relatively irreversibly and has high reactivity towards sulfur-containing amino acids such as methionine. TGA has been observed to form a crosslinked tissue that is less susceptible to calcification relative to glutaraldehyde crosslinked tissue, and TGA does not alter tissue mechanical properties as much as glutaraldehyde treatment. The properties of TGA crosslinked tissue are described further in Van Wachem et al. *J Biomed Mater Res* 2000; 53(1): 18-27 and Connolly, et al. *Am J Pathol* 2005; 166(1): 1-13, both of which are incorporated herein by reference.

Epoxyamines are molecules that generally include both an amine moiety e.g. a primary, secondary, tertiary, or quaternary amine, and an epoxide moiety. In general, the epoxyamine compound can be a monoepoxyamine compound and/or a polyepoxyamine compound. In some embodiments, a polyepoxyamine compound has at least two epoxide moieties and possibly three or more epoxide moieties.

In epoxyamines, the epoxide ring can be separated from the nearest amino moiety by between 1 and 5 atoms, i.e., a $C_1$-$C_5$ branched or linear alkyl or substituted alkyl chain, such as the methylene group, which separates the epoxide ring and the tertiary amine moiety in TGA. Other chemical groups which can be interposed between the epoxide ring and the nearest amino moiety include, for example, branched or linear alkenyl chains, substituted alkyl chains, ring groups and aromatic groups. The epoxyamine compounds can have high reactivity with a variety of functional groups including, for example, alcohols, amines, sulfur containing functional groups, such as thiols and the like.

Azide Esters

Free carboxyl groups on collagen can be converted into acyl azide groups, which react with free amino groups on adjacent side chains to crosslink the collagen tissue. This crosslinking approach is described in Petite, et al. *Biomaterials* 1995; 16(13): 1003-1008, incorporated herein by reference. Diphenylphosphoryl azide is another azide that is commonly used in the activation of free carboxyl groups on collagen to react with free amino groups to achieve crosslinking/stabilization in collagen tissue. See, Petite, et al, *J Biomed Mater Res* 1994, 28, 159-165, incorporated herein by reference. Published results suggest that azide ester treated tissues have the same resistance as glutaraldehyde-treated tissues to chemical solubilization by cyanogen bromide and to enzymatic digestion by collagenase, as described in Petite, et al. *J Biomed Mater Res* 1990; 24(2): 179-187, incorporated herein by reference.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein. All patents, patent applications, and publications referenced herein are hereby incorporated by reference herein to the extent that the incorporated material is not contrary to any of the explicit disclosure herein.

EXAMPLES

Example 1

Evaluate Devices Using Silicon Models

Figure 8:
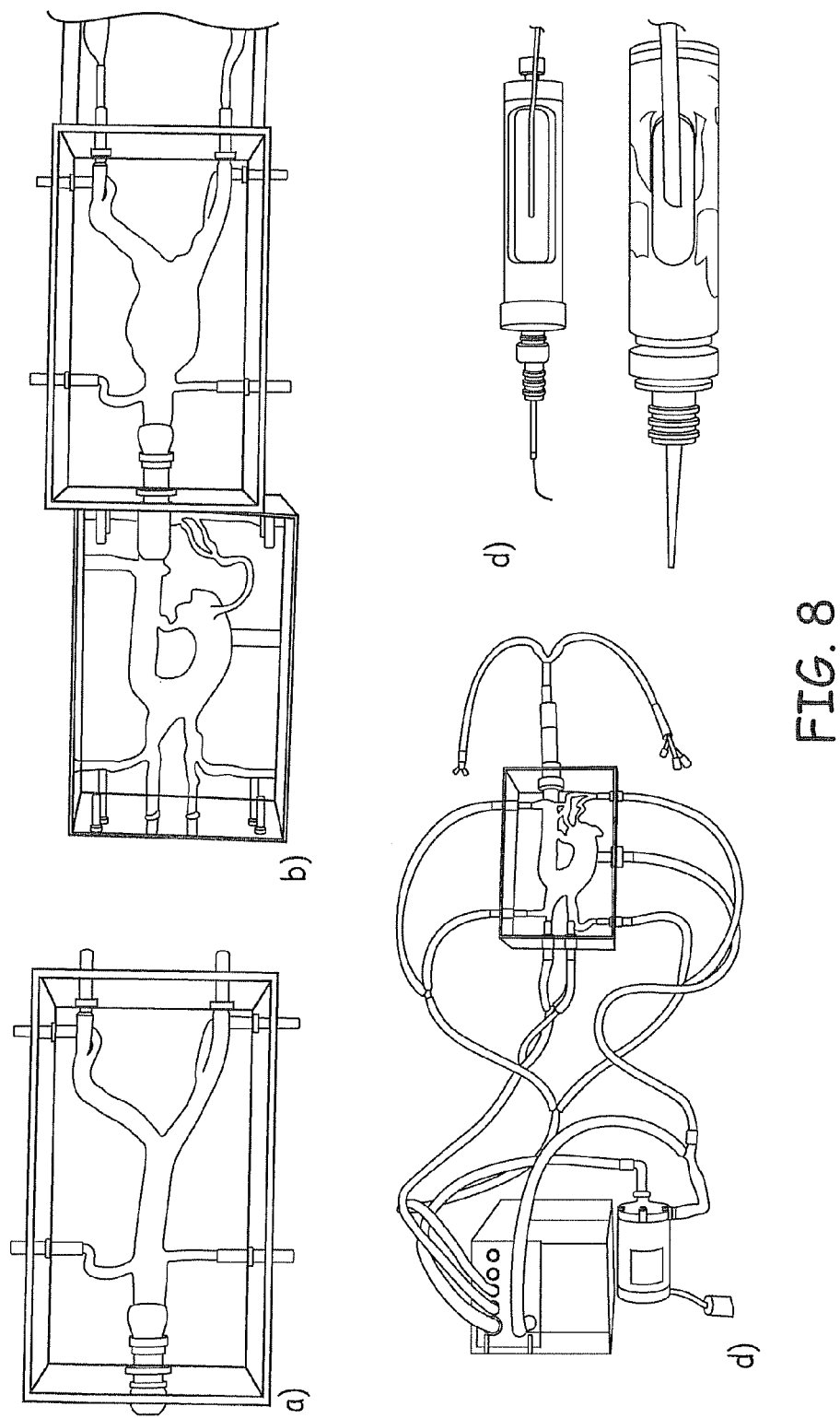
FIG. 8 is a diagram showing silicon models: (A) Silicon model of standard abdominal aorta. (B) Silicon model of a large abdominal aortic aneurysm; also shows the ability to add other parts of the vasculature to the system such as thoracic aorta and femoral arteries. (C) Model of thoracic aorta set up with pump system; this can be used to simulate blood flow and pressure. (D) Supplemental tools meant to simulate the percutaneous feel of device introduction.

A series of in vitro tests can be performed to evaluate the effectiveness of isolation at particular balloon pressures, the timing of the procedural steps and manipulations during use of the devices described herein. A device and procedure essentially as described with respect to FIGS. 1-7 can be used. Testing can be primarily performed with the assistance of a set of physiologically relevant silicon models, which are excellent mimics of the human anatomy. These models are made by Elastrat (Geneva, Switzerland) and are relatively soft and compliant, providing a fairly realistic feel for the deployment of endovascular devices in the actual vasculature. Elastrat models are available for the abdominal aorta (FIG. 8A), and more specifically for AAAs (FIG. 8B), and can be customized to include a significant portion of the femoral and iliac arteries. These models can be accompanied with a pump system that can regulate fluid flow, allowing the user to control simulated blood flow and pressure, as shown with a thoracic aorta model in FIG. 8C. Furthermore, percutaneous introducers are also available through Elastrat, which utilize a soft silicon material to mimic the percutaneous feel of device introduction (FIG. 8D).

The following steps can be performed: (1). Insert the introducer sheath of the device into the model femoral artery in the silicon model. (2). Guide distal tip of the catheter of the device to just inferior to renal artery branches of the model. (3). Deploy the extendable elements of the devices so as to create an isolated and 'closed' luminal region between these deployed extendable elements; the deployed extendable elements can be checked regarding the isolation of the vessel segment, which should be maintained isolated long enough to complete the entire procedure, which is estimated to be about 30 min. (4). Aspirate blood out of this isolated region, allowing for more concentrated delivery of therapeutic compositions such as PGG. (6). Deliver stabilizing agent (and subsequent rinses) to the lumen of isolated segment. (7). Aspirate stabilizing agent (and subsequent rinses) out of isolated region. (8). Optionally filling the isolated segment with blood. (9). Transform the deployed extendable elements to a low profile configuration and remove the device from the model femoral artery.

The following characteristics of the procedure can be evaluated: (1) Ease of deployment, which includes access through percutaneous introduction model (FIG. 8D), guidance of the distal end of the catheter of the device to appropriate area of aorta, and deployment of sealing elements. (2) Quality of sealing/isolation, when the silicon model is filled with colored fluids and exposed to 'blood pressure', the ability of the sealing elements to seal off isolated region for 30 min and prevent leakage in either direction of the sealing elements can be visualized with the colored fluids. (3). Aspiration, the colored fluid mimicking human blood, for example, porcine blood or other solution with similar viscosity, should be able to be easily aspirated out of isolated region through the fluid exchange lumen(s) of the device. Anticoagulant may be used in the fluid to prevent coagulation of the blood; (4). Delivery, the aneurysm stabilizing agent should be able to be easily pushed through the device in order to fill the majority of the isolated region created by the sealing elements; aspiration may be applied simultaneously to facilitate the distribution of the stabilizing agent. (5). Ease of removal, although no problems are foreseen, the device should be able to be easily removed from the silicon model, allowing for restoration of normal fluid (blood) flow after the treatment procedure.

Experience gained with the procedure involving the model vascular system can facilitate performance of large animal model studies, which are described in the following example.

Example 2

Evaluate Devices in Large Animal Model

The device can be evaluated, in a surgical setting, for its ability to isolate a given segment of infra-renal abdominal aorta and subsequent delivery of the stabilizing treatment. Pigs have traditionally been used as a model for endovascular aneurysm devices due to significant similarities with the relevant human vasculature. A device and procedure essentially as described with respect to FIGS. 1-7 can be used within adult pigs to directly deliver stabilizing agent to aortic wall. Following the treatment procedure, the porcine abdominal aorta can be exposed to an array of tests to evaluate the presence (binding) of the therapeutic agent such as PGG within the tissue, and its subsequent effect on the tissue.

Specifically, five adult male pigs can be anesthetized to gain access to the vasculature via the femoral artery. Radioopaque markers can be placed accordingly on the device so that angiography can be used during the treatment procedure to visualize device deployment and subsequent delivery of the therapeutic composition. The distal tip of the catheter of the device can be guided through an introducer sheath to access abdominal aorta and be placed just inferior to the renal arteries. The procedural steps outlined in Example 1 can be conducted.

PGG used in the example can be labeled with tritium ($^3$H) to form a radioactive compound that can be quantified with a liquid scintillation counter to confirm binding and delivery of PGG to the abdominal aorta. Labeled PGG can be obtained from American Radiolabeled Chemicals (St. Louis, Mo.), which specializes in customized radioactive compound labeling. Contrast agent can be added to the therapeutic composition cocktail containing the stabilizing agent to visualize the delivery procedure. Once the therapeutic composition resides in the isolated area for 20 minutes, the area can be aspirated and rinsed thoroughly, and the device can be removed from the vasculature. After the removal of the device, normal blood flow can be restored in the vasculature while the pigs are monitored under general anesthesia for about 30 minutes. After the monitoring, the animals can be euthanized and aortic tissue collected for analysis.

Abdominal aortic samples collected can then be analyzed for radioactivity. Once excised, tissues can be washed in buffered saline overnight, then digested in Solvable (Perkin-Elmer; Wellesley, Mass.). These digests can then be diluted in liquid scintillation fluid (Hionic-Fluour, Perkin-Elmer) and measured for tritium content. In addition to quantifying $^3$H-PGG within the abdominal aorta, the distribution of PGG throughout other neighboring tissues and organs can be analyzed. The analysis can provide insight as to how well PGG was delivered, and if any "leaching" of PGG may have occurred. As a result, tritium can also be quantified within excised thoracic aorta, heart, lungs, liver, and kidneys.

Other analysis can also be conducted on the excised tissue: Abdominal aorta collected after the procedure can be exposed to a battery of tests to confirm its binding and effectiveness on the tissue. For mechanical testing, circumferential strips of the treated aorta can be used for stress-strain analysis on a Chatillon TCD100 apparatus (Ametek; Largo, Fla.). For resistance to enzymatic degradation, samples of abdominal aorta (~1 cm×1 cm) can be subjected to an in vitro elastase digestion assay, as described previously the '834 patent. Histology on paraffin-embedded samples can be used to evaluate presence of PGG within the tissue, using a $FeCl_3$-based stain specific for polyphenols. For each of these studies, fresh untreated porcine abdominal aorta can be used as controls (n=5).

By conducting the treatment procedure in adult pig, the device is tested in a large animal with vasculature similar to that of humans. Long-term (chronic) studies in large animals and initiation of human studies can follow the initial animal test outlined above.

We claim:

1. A method for treating an isolated portion of a blood vessel, the method comprising:
   positioning an isolation device within the blood vessel wherein the isolation device comprises a sealing catheter and an introducer sheath, and the positioning of the isolation device comprises positioning the introducer sheath into the femoral artery in one of the legs of a patient and delivering the sealing catheter through the introducer sheath to place the first extendable element in the aorta, wherein the sealing catheter comprises a first extendable element, a first fluid exchange opening, a first fluid exchange lumen, and a first proximal connection port, wherein the introducer sheath comprises a second extendable element, a second fluid exchange opening, and a second fluid exchange lumen, wherein the extendable elements are movable relative to each other, wherein a first flow path extends from the first proximal connection port through the first fluid exchange lumen to the first fluid exchange opening of the sealing catheter, and wherein a second flow path extends from the second proximal connection port through the second fluid exchange lumen to the second fluid exchange opening of the introducer sheath;
   isolating the selected portion of the blood vessel by adjusting the relative positions of the extendable elements and extending the two extendable elements to contact the walls of the vessel to form the isolated portion;
   aspirating fluid from the isolated portion through the second flow path; and
   delivering a therapeutic composition to the isolated segment of the blood vessel through the first flow path after aspiration of fluid from the isolated portion of the blood vessel.

2. The method of claim 1 wherein the first extendable element is placed in the aorta below the renal arteries.

3. The method of claim 1 wherein an additional sealing device is deployed in the femoral artery in the other leg of the patient to isolate a "Y" shaped portion of the blood vessel along with the first and the second extendable elements.

4. The method of claim 3 wherein the additional sealing device is an introducer sheath and wherein an endovascular treatment device is delivered into the isolated section of the blood vessel through the additional sealing device.

5. The method of claim 1 wherein the therapeutic composition comprises a phenolic elastin stabilizing composition.

6. The method of claim 1 wherein the therapeutic composition further comprises a distinct collagen crosslinking agent.

7. The method of claim 1 wherein the isolated portion of the blood vessel comprises an aneurysm.

8. The method of claim 7 wherein the volume of the aneurysm is reduced following aspiration by at least about 10 percent wherein the volume of the aneurysm is evaluated as the excess volume in comparison with a corresponding healthy vessel lacking an aneurysm.

9. The method of claim 1 wherein the therapeutic composition further comprises a contrast agent.

10. The method of claim 1 wherein the step of delivering the therapeutic composition is repeated with a different composition, wherein the delivery of one therapeutic composition comprises the delivery of an elastin stabilization composition and the delivery of the other therapeutic composition comprises the delivery of a collagen stabilization composition.

11. The method of claim 10 wherein the collagen stabilization composition comprises glutaraldehyde, carbodiimides, photo-oxidation agent, genipin, epoxies, or azide esters.

12. The method of claim 1 further comprising a pretreatment step before the delivery of the therapeutic composition wherein the pretreatment step comprises the delivery of a thrombolytic composition to break up thrombus in the isolated blood vessel.

13. The method of claim 10 wherein the aspiration and delivery steps can be performed at least partially simultaneously with the rate of aspiration consistently greater than the delivery.

14. The method of claim 1 wherein the first extendable element is a compliant balloon with concaved ends that is positioned at or near the distal end of the sealing catheter and is inflated through a first balloon inflation lumen in the sealing catheter to make compliant contact with the wall of the aorta.

15. The method of claim 1 wherein the second extendable element is a sealing balloon attached on the distal end of the introducer sheath and is inflated through a second balloon inflation lumen in the introducer sheath to make contact with the wall of femoral artery and wherein the isolated portion of the blood vessel is created between the compliant balloon of the sealing catheter and the sealing balloon of the introducer sheath.

* * * * *